United States Patent [19]
Maat et al.

[11] Patent Number: 5,529,926
[45] Date of Patent: Jun. 25, 1996

[54] CLONING AND EXPRESSION OF DNA ENCODING A RIPENING FORM OF A POLYPEPTIDE HAVING SULFHYDRYL OXIDASE ACTIVITY

[75] Inventors: Jan Maat, Monster; Wouter Musters, Maassluis; Hein Stam, Diemen; Peter J. Schaap, Hoorn; Peter J. van de Vonderwoort; Jacob Visser, both of Wageningen; Johannes M. Verbakel, Maasland, all of Netherlands

[73] Assignee: Unilever Patent Holdings BV, Netherlands

[21] Appl. No.: 423,441

[22] Filed: Apr. 19, 1995

Related U.S. Application Data

[63] Continuation of Ser. No. 44,620, Apr. 9, 1993, abandoned.

[30] Foreign Application Priority Data

Apr. 10, 1992 [EP]  European Pat. Off. .............. 92201027

[51] Int. Cl.⁶ ..................................................... C12N 1/20
[52] U.S. Cl. ..................... 435/252.3; 435/6; 435/69.1; 435/189; 435/240.2; 435/320.1; 536/22.1; 536/23.1; 536/23.2; 536/23.7
[58] Field of Search .............................. 435/6, 69.1, 189, 435/240.2, 252.3, 320.1; 536/22.1, 23.1, 23.2, 23.7

[56] References Cited

U.S. PATENT DOCUMENTS 4,632,905  12/1986  Starnes et al. .......................... 435/189
4,894,340   1/1990  Hammer et al. ........................ 435/189

FOREIGN PATENT DOCUMENTS 0321811   6/1989  European Pat. Off. ..

OTHER PUBLICATIONS

Janolino et al., "A comparison of sulfhydryl oxidases from bovine milk and from Aspergillus niger", Milchwissenschaft, vol. 47, No. 3, Mar. 1992, Munich, Germany, pp. 143–146.

Janolino et al., "Confirmation of a blocked amino terminus of sulfyhdryl oxydase", Journal of Dairy Science vol. 73, No. 9, Sep. 1990, U.S., pp. 2287–2291.

De La Motte et al., "Aspergillus niger sulfhydryl oxidase", Biochemistry, vol. 26, No. 23, 17 Nov. 1987, Easton, PA, U.S., pp. 7363–7371.

Glover "Principles of Cloning DNA" *Gene Cloning* pp. 1–20 1984.

*Primary Examiner*—Robert A. Wax
*Assistant Examiner*—Hyosuk Kim
*Attorney, Agent, or Firm*—Cushman Darby & Cushman

[57] ABSTRACT

The invention relates to recombinant DNA technology for the production of an enzyme having sulfhydryl oxidase ("SOX") activity. This SOX-enzyme can be used where the oxidation of free sulfhydryl groups (thio compounds) to the corresponding disulfides is desirable. SOX enzyme may be used for treatment of bakery products or for removal of off-flavour from milk or beer.

6 Claims, 18 Drawing Sheets

N-terminal amino acid sequence of A.niger SOX and derived oligonucleotides.

NH2- Ser- ? -Ile-Pro-Gln-Thr-Asp-Tyr-Asp-Val-Ile-Val-Val-Gly-Gly-Gly-Pro-Ala-Gly-etc.
(SEQ ID NO: 3)

SOX04WM

SOX05WM

SOX04WM: 5'-TGY ATH CCI CAR ACI GAY TAY GAY GT-3'  (SEQ ID NO: 10)

SOX05WM: 5'-ATY CCY CAG ACY GAC TAC GAC GTI ATY GTI GTI GGI GGI GGI CCY GCY GG-3'  (SEQ ID NO: 11)

(R=G of A; Y=C of T; H=A,T of C; N=G,A,T of C; I=inosine)

Fig. 2B

Amino acid sequence of CNBr fragment #9 and derived oligonucleotides (Met)#Val-Asp-Asn-Lys-Ile-Asp-Thr-Thr-Asp-Tyr-Thr-Gly-(Met)  (SEQ ID NO: 4)

SOX06WM, SOX07WM →
SOX08WM, SOX09WM →

SOX06WM: 5'-GT RTA RTC IGT IGT RTC IAT YTT RTC IAC CAT-3'  (SEQ ID NO: 12)

SOX07WM: 5'-GT RTA RTC NGT NGT RTC NAT YTT RTC NAC CAT-3'  (SEQ ID NO: 5)

SOX08WM: 5'-GT RTC IAT YTT RTT RTC IAC CAT-3'  (SEQ ID NO: 13)

SOX09WM: 5'-GT RTC NAT YTT RTT RTC NAC CAT-3'  (SEQ ID NO: 6)

(R=G of A; Y=C of T; H=A,T of C; N=G,A,T of C; I=inosine)

Fig.3.

SOX production by filamentous fungi

| Experiment # | Strain | Biomass [g dry weight] | SOX activity [U/g dry weight] |
|---|---|---|---|
| 1 | A.niger N400 (CBS 120.49) | 39 | 23.1 |
| 2 | A.sojae ATCC 20388 | 74 | 15.9 |
| 3 | A.oryzae ATCC 91002 | 88 | 0.1 |
| 4 | A.sojae ATCC 20235 | 50 | 12.1 |
| 5 | A.tubigensis CBS 115.29 | 36 | 56.0 |
| 6 | P.lilanicum CBS 284.36 | 59 | 0.3 |
| 7 | A.,tubigensis CBS 161.79 | 62 | 1.5 |
| 8 | A.niger var. awamori CBS 115.52 | 98 | 4.3 |

T = Aspergillus tubigensis CBS 115.29
N = Aspergillus niger N400 (CBS 120.49)
A = Aspergillus niger var. awamori CBS 115.52
S = Aspergillus sojae ATCC 20235
Ni = Aspergillus nidulans WG096

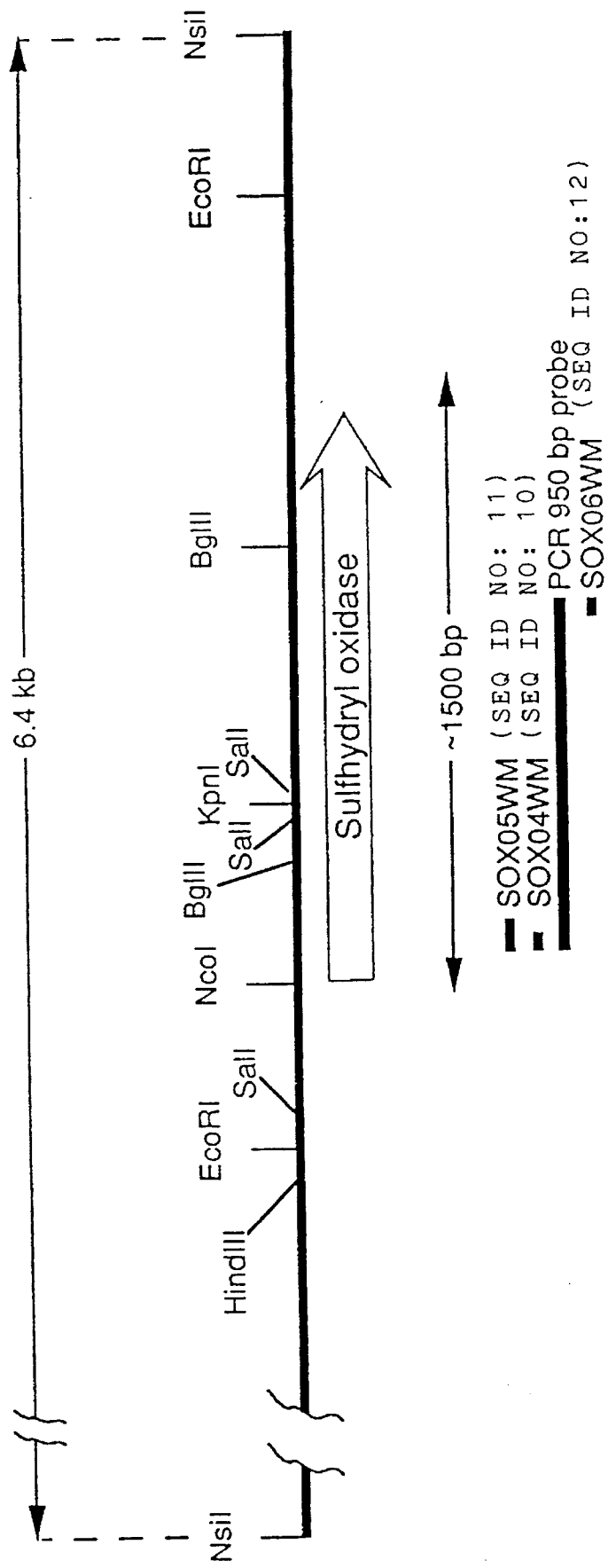

Fig. 7A

Sequence listing

SEQ ID NO: 1

SEQUENCE TYPE: Nucleotide with corresponding polypeptide

SEQUENCE LENGTH: 2563 base pairs

STRANDNESS: double

TOPOLOGY: linear

MOLECULE TYPE: genomic DNA

ORIGINAL SOURCE ORGANISM: Aspergillus niger

IMMEDIATE EXPERIMENTAL SOURCE: pUR7500 and pUR7501 in E.coli JM109 (CBS 196.92 and CBS 197.92)

FEATURES:  from    1 to  476 bp: promoter from  477 to  533 bp: signal sequence from  534 to  702 bp: exon 1 from  703 to  769 bp: intron 1 from  770 to 1573 bp: exon 2 from 1574 to 1681 bp: intron 2 from 1682 to 1827 bp: exon 3 from 1828 to 1830 bp: stop codon from 1831 to 2563 bp: 3'-flanking sequences

PROPERTIES: Aspergillus niger sulfhydryl oxidase (sox) gene

Fig. 7B

```
  1 GCATCTGGGC CCTCTTCCAC TTGCATGCAC TATTGAAATC CCAGCCCTGC CGATCGAATT  60
 61 CCGCCGATCT TGGCAGCATC CAACCGGGAT TTGAAGCCAC TGCAGTCATC GACTCTCATT 120
121 CGGCAGGTCG ACTCTAGTCT CCCCAACCAT ATTCTCAATA ATCTTCTCTT TACCTTGGCA 180
181 CGGGGACCC CGAACTGGAC TGGCACGGAA TCGATCGTGT CGATCCCCTT CAGCTGCTCC 240
241 ACCAGCTCGA GTCTTGGCTG CATCCCAGCT GAATCACCAA ATCCTGCTCC TCGGCCTCGG 300
301 ACAACTTGGG ACGATGTGCG TGCTGCACTG TCCCTTGAGG AACATGCTGT TGTGGAGGTA 360
361 ACAACTTGGG TTGAAAGCTG CTGCTGCTGC TGCATCTTCT TCTCGGCAGA CTGCAGCAGG 420
421 CCTTCTCTCT TCTTCAGTGC GTGGGGAACG ATCCGATCCG TAACCTAGTC CACACC       476

477
ATG GCT CCC AAG TCC CTC TTT TAT TCC CTC TTC TCC ACC ATC AGC GTC GCT CTG GCG TCG
Met ala pro lys ser leu phe tyr ser leu phe ser thr ile ser val ala leu ala ser
-19                 -15                 -10                  -5                  -1 +1

537
TCC ATC CCC CAG ACC GAT TAC GAT GTG ATT GTC GTG GGA GGA GGT CCC GCG GGC CTC AGT
ser ile pro gln thr asp tyr asp val ile val val gly gly gly pro ala gly leu ser
              5                  10                  15                  20

597
GTC TTG AGC AGT CTC GGG CGC ATG AGA CGG AAG ACC GTG ATG TTC GAC TCG GGA GAA TAC
val leu ser ser leu gly arg met arg arg lys thr val met phe asp ser gly glu tyr
             25                  30                  35                  40

657
CGT AAT GGT GTT ACG CGC GAG ATG CAC GAT GTC CTT GGC TTT GAT G
arg asn gly val thr arg glu met his asp val leu gly phe asp
             45                  50                  55

GTAATTTC TGCCTCATTT 720
703 ACCCCAGGAT CTCCCATTTC ATGTCAATTT ATACCTAACA TCCACAAAG            769
```

Fig. 7C

```
770
  GC ACT CCA CCT GCC CAA TTC CGT GGC CTC GCC CGC CAG CAG ATC TCT AAA TAC AAC TCG
  gly thr pro pro ala gln phe arg gly leu ala arg gln gln ile ser lys tyr asn ser
          60                          65                          70              75

829
  ACC AGC GTC ATC GAC ATC AAG ATC ATC GAC TCC ATC ACC CCG GTC GAG GAT GCC GCA GCC AAC
  thr ser val ile asp ile lys ile ile asp ser ile thr pro val glu asp ala ala ala asn
          80                          85                          90              95

889
  AGC TCA TAC TTC CGT GCC GTC GAC GCC AAC GGC ACA CAA TAC ACC TCC CGC AAG GTA GTC
  ser ser tyr phe arg ala val asp ala asn gly thr gln tyr thr ser arg lys val val
          100                         105                         110             115

949
  CTG GGT ACC GGG CTG GTC GAC GTG ATC CCT GAT GTG CCC GGT CTC CGC GAA GCC TGG GGC
  leu gly thr gly leu val asp val ile pro asp val pro gly leu arg glu ala trp gly
          120                         125                         130             135

1009
  AAG GGC ATC TGG TGG TGT CCC TGT GAC GGC TAC GAG CAC CGC GAC GAG CCC CTC GGT
  lys gly ile trp trp cys pro cys asp gly tyr glu his arg asp glu pro leu gly
          140                         145                         150             155

1069
  ATC CTA GGT GGG TTG CCG GAC GTG GTC GGC AGC GTC ATG GAA GTC ACC CAC ACC CTG TAC TCG
  ile leu gly gly leu pro asp val val gly ser val met glu val thr his thr leu tyr ser
          160                         165                         170             175

1129
  GAC ATC ATC GCT TTC ACT AAC GGC ACC TAC ACG CCC GCC AAC GAA GTC GCC CTG GCA GCC
  asp ile ile ala phe thr asn gly thr tyr thr pro ala asn glu val ala leu ala ala
          180                         185                         190             195
```

Fig. 7D

```
1189
AAG TAC CCG AAC TGG AAG CAG CAG CTC GAA GCG TGG AAT GTC GGT ATT GAC AAC CGC TCC
lys tyr pro asn trp lys gln gln leu glu ala trp asn val gly ile asp asn arg ser
            200                         205                         210                         215

1249
ATT GCA TCC ATT GAG CGT CTC CAA GAT GGA GAT GAC CAC CGC GAC GAC ACG GGT AGA CAG
ile ala ser ile glu arg leu gln asp gly asp asp his arg asp asp thr gly arg gln
            220                         225                         230                         235

1309
TAC GAC ATC TTC CGG GTC CAT TTC ACC GAT GGC TCC AGC GTT GTA CCG AAC ACC TTC ATC
tyr asp ile phe arg val his phe thr asp gly ser ser val val pro asn thr phe ile
            240                         245                         250                         255

1369
ACA AAC TAC CCG ACC GCC CAG CGT TCC ACT CTG CCC GAG GAA CTG AGC CTG GTC ATG GTG
thr asn tyr pro thr ala gln arg ser thr leu pro glu glu leu ser leu val met val
            260                         265                         270                         275

1429
GAT AAC AAG ATC GAT ACG ACA GAC TAC ACG GGC ATG CGC ACC AGT CTG TCG GGC GTC TAC
asp asn lys ile asp thr thr asp tyr thr gly met arg thr ser leu ser gly val tyr
            280                         285                         290                         295

1489
GCC GTC GGT GAC TGC AAC AGT GAT GGA TCC ACG AAC GTG CCG CAT GCC ATG TTC AGC GGA
ala val gly asp cys asn ser asp gly ser thr asn val pro his ala met phe ser gly
            300                         305                         310                         315

1549
AAG AGA GCG GGT GTC TAT GTG CAT G
lys arg ala gly val tyr val his
            320
```

Fig. 7E

```
1574                   GTGAGCC TCCCTATACC TTCCTGTCTT CCGTCTCTTT TTTTTTTC 1620
1621 CCCCTTTCTT CCATCCCTAC CATGAGATCT TGAATGAAAG TCAACTAACA AAACGTGTA 1680
1681 G                                                                1681

1682
TG GAA ATG TCC CGC GAA GAG TCC AAC GCG GCC ATC TCC AAG CGC GAC TTC GAC AGA CGC
val glu met ser arg glu glu ser asn ala ala ile ser lys arg asp phe asp arg arg
   325                         330                         335                         340

1741
GCC CTG GAG AAG CAA ACC GAG CGC ATG GTC GGC AAT GAG ATG GAG GAT CTG TGG AAG CGC
ala leu glu lys gln thr glu arg met val gly asn glu met glu asp leu trp lys arg
   345                         350                         355                         360

1801
GTG CTG GAG AAC CAC CAC CGC CGG TCT TGA
val leu glu asn his his arg arg ser STOP
   365                         370    373

ATCTTCCATA CTATATACTA ACGTCCTGTC 1860
1831 CATGAATAAA CAACACGACT AGCCACTATG ATATATAAAT TTATATGTAA CTAACGTTTA 1920
1861 ACGTCCTCCA TGATCATATG GAGTGACACA CATATTAATA CTTTCACCAA GAAAAATACA 1980
1921 TACATACACA CGCATTCGGT AATAAAACAT AGCTCCTGGG TATCTACATA GTAAGCAATT 2040
1981 CCGTAACTCT AAATAATGCC AACTCTAGTA CTTGGATTGC CAGGTTGGTA GGTTAGCTAC 2100
2041 TTCAGTAGTA ACTGAATCGA CGCACCCCAA CAACAAAGTA AGTACCTCCT ACCTCCCACC 2160
2101 CACTTTACCA AGCACCCAGA AATCAACAAA TGAAAGAGAA ATACGATTAA TAGTGACAAC 2220
2161 CTGAAATTAC ATTATACAGG TCATATCGGC TTGTCTTGAT TCGTACTTTT AGCTAATACC 2280
2221 TTGTGAAACT CCAAGAATAC CTAGTAGTAG TTGAGACTGT GACTCGGAAG TTGTCTGGTC 2340
2281 CAAATTATAT ATATCGACTA ATGTTAAAAG CACTCTTCCA ACAATACTAG TAGTACCTAA 2400
2341 TGAATAGAAC TATAGCTAAG TACTACTAGT CATTGTATGA CTTTATTTGG GTTTATCTAT 2460
2401 ACTACCGTAG TACTACTAGT TACTACGAGT TTGAATGGAT AAATACTTAC TGCTATAAAG 2520
2461 GCCGAAGGGG GGTGGATTGT GGGATGTTTC TGTGTCAGAA TTC             2563
```

Southern analysis of HindIII digestions of total genomic DNA

Lanes a: 5 μg DNA

Lanes b: 0.5 μg DNA, loaded onto the gel 20 min. prior to lanes a

Note: not all sites for each restriction enzyme are shown

Note: not all sites for each restriction enzyme are shown

CLONING AND EXPRESSION OF DNA ENCODING A RIPENING FORM OF A POLYPEPTIDE HAVING SULFHYDRYL OXIDASE ACTIVITY

This is a continuation of application Ser. No. 08/044,620, filed on Apr. 9, 1993, which was abandoned upon the filing hereof.

The present invention relates to the field of recombinant DNA technology and more in particular relates to its use in view of the biotechnological production of a polypeptide having sulfhydryl oxidase activity.

A polypeptide having sulfhydryl oxidase activity is a polypeptide that can be used in any context where the oxidation of free sulfhydryl groups to disulfide bonds is desirable, such as the preparation of a bakery product or the removal of off-flavour from milk or beer.

BACKGROUND OF THE INVENTION

Sulfhydryl oxidase (SOX) is an enzyme known to catalyze the conversion of thio compounds to the corresponding disulfides according to the equation: $2R\text{-}SH + O_2 \rightarrow R\text{-}S\text{-}S\text{-}R + H_2O_2$. SOX is therefore of interest in applications where oxidation of free sulfhydryl groups to disulfide linkages is sought.

Non-specific oxidants such as hydrogen peroxide, peracids, borates, bromides, etc. which have been employed heretofore for effecting disulfide bond formation are disadvantagous as unwanted side reactions may occur. In contrast enzyme catalyzed reactions, such as the oxidation of free sulfhydryls by the enzyme SOX, can provide the selectivity desired avoiding side reactions. For example the flavour problems caused by non-specific oxidants due to oxidation of other components of a food system can be eliminated due to the specificity of an enzyme catalyzed reaction. Further advantages of SOX are that SOX oxidizes under milder conditions than non-specific oxidants, which is useful in food systems, and that the use of highly acidic, highly basic or high temperature conditions in food systems is not required for SOX activity. In contrast such conditions are necessary when non specific oxidants are used and such conditions may have an adverse effect on the organoleptic quality of the food system. Furthermore an enzyme catalyzed oxidation will also usually have a greater velocity than an oxidation catalyzed by a non-specific oxidant.

One example of a process in which treatment with sulfhydryl oxidase is of value is the removal of a burnt flavour from Ultra-High Temperature (UHT) sterilized milk. For details of such usage of SOX, reference is made to U.S. Pat. Nos. 4,087,328 and 4,053,644.

Another example of a process in which treatment with sulfhydryl oxidase is beneficial is a process in which SOX is employed as a dough conditioner to act on free sulfhydride groups in contrast to non-specific oxidants. In U.S. Pat. No. 4,894,340 it is suggested that *Aspergillus niger* SOX could improve the rheological properties of dough and provide an improvement in the form and texture of a baked product.

SOX derived from a mammalian (bovine) source can be used in a process for removal of burnt flavour from milk but does not exhibit beneficial effects in a wheat flour dough [Kaufman et al. Cereal Chem. 64 (3): 172–176]. Microbially derived SOX can be used in both processes.

Several enzymes derived from both mammalian and microbial sources having the ability to catalyze the conversion of thio compounds to the corresponding disulfides according to the equation: $2R\text{-}SH + O_2 \rightarrow R\text{-}S\text{-}S\text{-}R + H_2O_2$ have been reported in the scientific literature.

In 1975 Janolino and Swaisgood purified an iron-dependent sulfhydryl oxidase from bovine milk, said oxidase demonstrated activity toward GSH, cysteine, dithiothreitol, 2-mercaptoethanol and reduced ribonuclease A. Milk extracts from other sources, including a human source [Isaacs C. E. et al., Pediatr. Res. 18:532 (1984)] have also been reported to exhibit sulfhydryl oxidase activity.

Further sources of sulfhydryl oxidase that have been reported are kidney homogenates and mammalian pancreas tissue [Clare D. A. et al., Arch. Biochem. Biophys. 230:138 (1984)].

Sulfhydryl oxidase activity has also been discovered in rat epididymal fluid [Chang T. S. K. and Morton B., Biochem. Biophys. Res. Commun. 66:309 (1975)]. The best substrates for this sulfhydryl oxidase were reported to be dithiothreitol, GSH and cysteine. As in the case of the skin and bovine milk enzymes, this rat enzyme was capable of reactivating reduced ribonuclease A.

Mammalian source SOX e.g. as mentioned in the U.S. Pat. Nos. 4,087,328 and 4,053,644 has the disadvantage that it is not available in large quantities at economic prices and furthermore cannot be used in a process for improving a dough.

Therefore research has been directed at a microbial source that could possibly provide a readily available commercially attractive supply of SOX. Various microbial sources of sulfhydryl oxidase-are known.

In 1956 Mandels G. R., J. Bacteriol, 52:230 (1956) reported that the spores of the fungus *Mirothecium varrucaria* contained a sulfhydryl oxidase which catalyzed the oxidation of reduced glutathione (GSH), cysteine and homocysteine with concomitant reduction of $H_2O_2$.

In 1975 Olson J. A. [Ph.D. dissertation, University of Iowa (1976)] isolated a sulfhydryl oxidase from the culture fluid of an organism believed to be *Dactylium dendroides*. This copper metallo enzyme was found in mycelium extracts which also contained galactose oxidase. Olson reported that the purified sulfhydryl oxidase was capable of reactivating reductively denatured galactose oxidase.

Microbial SOX can be isolated from commercial enzyme preparations comprising SOX as a side product or contaminant obtained from microorganisms known to produce SOX. Examples of such commercial enzyme preparations are Fungamyl$^R$, Pectinex$^R$, and some amyloglucosidases However, separation costs and yield loss in purification and/or concentration of the SOX make the SOX product from such sources prohibitively expensive.

It is clear that separation costs and yield loss in purification and/or concentration of SOX recovered from the culture medium of a microorganism or from the microorganism itself will be uneconomical when such a microorganism is only capable of moderate levels of SOX production.

In U.S. Pat. No. 4,632,905 of Starnes et al. it is claimed that the microbial species *Aspergillus sojae, Aspergillus niger, Aspergillus oryzae, Bacillus subtilis,* and *Penicillium lilacinum* produce SOX at levels high enough for potential recovery of SOX. Starnes at al. also reported that very low levels of SOX elaboration were detected for *Bacillus licheniformis, Bacillus coagulans, Bacillus acidopullulyticus, Bacillus stearothermophilus, Mucor miehei,* and *Trichoderma reesei.* Subsequently they described that in particular it was possible to recover high unit activity SOX products through cultivation of *Aspergillus sojae.*

They describe that the oxidase was elaborated both intracellularly and extracellularly in recoverable quantities when the microorganism was cultivated. The cells could be easily removed from the whole broth (by conventional methods, e.g., centrifugation) and the cell-free broth could be filtered and usually concentrated by diafiltration with an overall recovery of about 40%. The SOX enzyme could also be recovered from the cells in similar overall yields by the same recovery protocol following rupturing of the microbial cell by high pressure disruption, sonication, enzymatic digestion or simply by cell autolysis. In general the same methods heretofore employed to liberate and produce solutions of other intracellular fungal enzymes from various Aspergillus species were used.

In U.S. Pat. No. 4,894,340 of Hammer et al., 1990, an isolated sulfhydryl oxidase enzyme derived from *Aspergillus niger* is described. This microbial SOX is characterized by a pH-optimum of about 5.5. The method for recovering said *Aspergillus niger* SOX is similar to the method described in the cited Starnes patent and comprises cultivating a SOX producing strain of the fungus, recovering SOX from the fungus, and purifying the recovered SOX. The recovery of SOX can be accomplished by lysing the cells by enzymatic digestion or other suitable means and precipitating the resulting proteins, or by suspending *A. niger* in brine of sufficient strength to partition the enzyme into the brine solution.

The present methods of obtaining sulfhydryl oxidase of mammalian origin are too lengthy, complex and expensive for economically feasible production of the enzyme.

From the literature the only apparent economically feasible sources of microbial sulfhydryl oxidase are *Aspergillus sojae* and *Aspergillus niger*. In practice however no commercial preparations of pure sulfhydryl oxidase are available. The production and purification of the product are still too complex and costly.

The subject invention is aimed at solving the abovementioned problems and is directed at the production of mammalian or microbial forms of sulfhydryl oxidase in a process that is economical and can lead to easier production of pure forms of the desired enzyme. Furthermore, with the process according to the invention it is possible to produce large amounts of many different forms of sulfhydryl oxidases that could not be produced previously. It is also possible to obtain sulfhydryl oxidases from *Aspergillus niger* and *Aspergillus sojae* in larger amounts and requiring less purification than has been described in the cited U.S. Patents.

SUMMARY OF THE INVENTION

The present invention is directed at providing recombinant DNA material comprising DNA with at least a nucleotide sequence encoding a ripening form of a polypeptide having sulfhydryl oxidase activity.

It is also an object of the present invention to provide a cell capable of expression, preferably capable of overexpression of a ripening form of a polypeptide having sulfhydryl oxidase activity encoded on recombinant DNA material.

The recombinant DNA material comprising a nucleotide sequence encoding a ripening form of a polypeptide having sulfhydryl oxidase activity can comprise a nucleotide sequence derivable from an organism that is homologous to the expression host cell into which cell said nucleotide sequence is incorporated or said nucleotide sequence can be heterologous to the expression host cell.

The expression of the nucleotide sequence encoding a ripening form of a polypeptide having sulfhydryl oxidase activity can be regulated by operably linking said nucleotide sequence to regulatory sequences that control a gene native to the organism from which said nucleotide sequence has been derived. The regulatory sequences can also be foreign i.e. derived from an organism belonging to a different strain, variety, genus or group of organisms than the organism from which the nucleotide sequence encoding a polypeptide with sulfhydryl oxidase activity has been derived. The regulatory regions can be regulatory regions of a sulfhydryl oxidase gene or regulatory regions of other genes.

Another preferred embodiment of the invention is a cell capable of overexpression and secretion of a ripening form of a polypeptide having sulfhydryl oxidase activity, preferably a mature form.

It is yet a further object of the present invention to provide a method for the production of a ripening form of a polypeptide having sulfhydryl oxidase activity which may in turn advantageously be used in an industrial process, such as the preparation of a bakery product or the removal of off-flavour from a food product in general, in particular such as milk or beer. The invention is also directed at sulfhydryl oxidase comprising products suitable for use in such processes.

A polypeptide having sulfhydryl oxidase activity according to the invention can also be used in other products, i.e. personal products in which a component is desired with the ability to form disulfide linkages by oxidation of free sulfhydryl groups. A polypeptide having sulfhydryl oxidase activity according to the invention can be used in general in a product for reinforcing the structure of proteins or proteinaceous structures, in particular in various products for the treatment of hair such as perming lotions shampoos or conditioners, for example as decribed in Japanese Patent Application 90-287815/38 of Kanebo KK.

BRIEF DESCRIPTION OF THE FIGURES

FIG. 3: Production levels of sulfhydryl oxidase activity by various strains of filamentous fungi under standardized conditions.

FIG. 6: Restriction map of the genomic DNA of *A. niger* in the region comprising the sox gene.

FIG. 7: Nucleotide sequence of the *A. niger* sox gene and amino acid sequence derived therefrom (SEQ ID NO: 1).

DETAILED DESCRIPTION OF THE INVENTION

Figure 1:
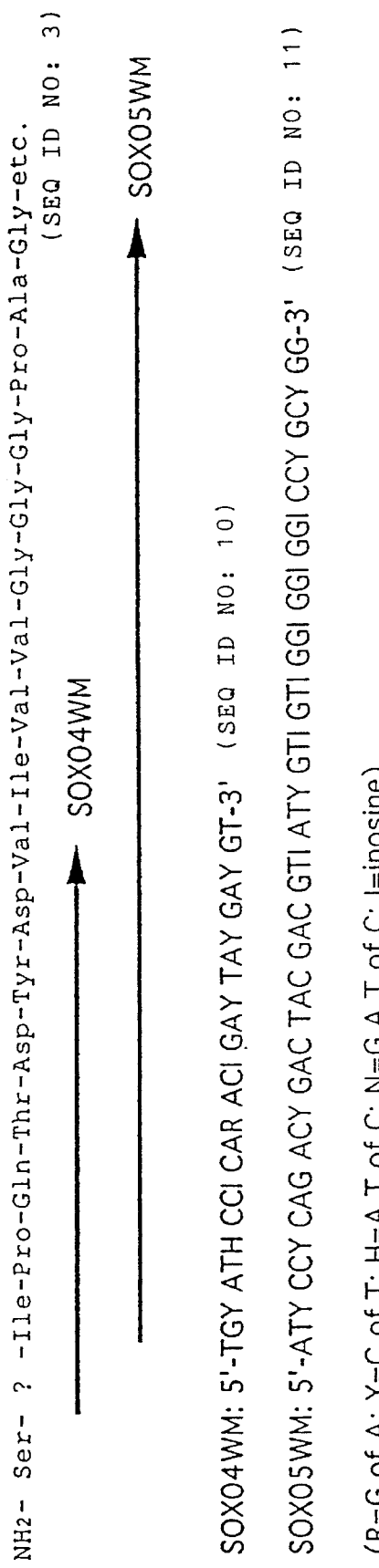
FIG. 1: Partial amino-terminal amino acid sequence of mature *Aspergillus niger* sulfhydryl oxidase and sequence of derived degenerate mixtures of synthetic oligonucleotides

The present invention is directed at a recombinant DNA material comprising at least a part of a nucleotide sequence encoding a ripening form of a polypeptide having sulfhydryl oxidase activity and genetic variants thereof.

The term "recombinant DNA material" can comprise a DNA molecule, or a mixture of various DNA fragments/molecules.

The term "genetic variants" as used herein includes hybrid DNA sequences comprising at least a part of a nucleotide sequence encoding a ripening form of a polypeptide having sulfhydryl oxidase activity optionally coupled to regulatory regions such as promoter, secretion and terminator signals originating from homologous or heterologous organisms. The term "genetic variants" also includes DNA sequences encoding mutant sulfhydryl oxidase polypeptides and degenerate DNA sequences encoding polypeptides wherein the sulfhydryl oxidase activity is retained.

The present invention also includes recombinant DNA material comprising at least a part of a nucleotide sequence capable of hybridizing to at least a part of the nucleotide sequence encoding a ripening form of a polypeptide having sulfhydryl oxidase activity and genetic variants thereof as described above which may differ in codon sequence due to the degeneracy of the genetic code or cross species variation.

The term "ripening form" refers to any of the different forms in which an enzyme may occur after expression of the associated gene. More in particular it refers to both the naturally and not naturally occurring mature form of an enzyme that can result after cleavage of a "leader" peptide and also to any form of an enzyme still comprising a "leader" peptide in any form. In general a "leader peptide" can be a prepro peptide, a pre peptide or a pro peptide.

The recombinant DNA material according to the invention can comprise at least a part of a nucleotide sequence encoding a ripening form of a polypeptide having sulfhydryl oxidase activity wherein said nucleotide sequence can be derived from any organism varying from a mammal to a microorganism. The origin of the nucleotide sequence can be selected depending on the application of the polypeptide that is produced by the recombinant DNA material according to the invention. As already stated in the introductory part, bovine sulfhydryl oxidase can be used for removing off-flavour from UHT milk but cannot be used for exhibiting beneficial effects in a wheat flour dough.

With a view to application in processes directed at the production of foodstuffs, a preferred recombinant DNA material according to the invention will comprise a nucleotide sequence encoding a ripening form of a polypeptide having sulfhydryl oxidase activity originating from a foodgrade organism.

As already stated the nucleotide sequence encoding a ripening form of a polypeptide having sulfhydryl oxidase activity can be of microbial origin. Such a sequence can be derived from a microorganism such as a fungus or a bacterium, preferably a foodgrade fungus or bacterium. Suitable fungi are the filamentous fungi e.g. the group comprising the genera Aspergillus, Trichoderma, Neurospora, Penicillium and Mucor. Of the genus Aspergillus the species of the group comprising *Aspergillus niger*, *Aspergillus awamori*, *Aspergillus oryzae*, *Aspergillus sojae*, *Aspergillus tubigensis*, *Aspergillus aculeatus* and *Aspergillus japonicus* are eminently suitable examples of organisms from which a nucleotide sequence encoding a ripening form of a polypeptide having sulfhydryl oxidase activity can be derived.

A suitable bacterium is a Bacillus bacterium for example a bacterium belonging to the group comprising *Bacillus subtilis*, *Bacillus coagulans*, *Bacillus acidopululiticus*, *Bacillus stearothermophylus*, *Bacillus licheniformis* and *Bacillus brevis*. Preferably the bacterium will be a gram positive foodgrade bacterium.

Sulfhydryl oxidase activity has been found in a number of strains and derivatives of the genus Aspergillus. e.g. *Aspergillus niger* N400 (CBS 120.49), *Aspergillus niger* var. awamori (CBS 115.52), *Aspergillus oryzae* (ATCC 91002) *Aspergillus sojae* (STCC 20388), *Aspergillus sojae* (ATCC 20235), *Aspergillus tubigensis* (CBS 11529), *Aspergillus tubigensis* (CBS 16179) and *Aspergillus japonicus* var. aculeatus (CBS 115.80), *Aspergillus japonicus* var. aculeatus (CBS 17266). In a number of strains successful hybridisation has taken place between the DNA isolated from *Aspergillus niger* and DNA of various other organisms as is demonstrated in FIG. 5.

A more concrete preferred embodiment of this aspect of the invention is recombinant DNA material comprising at least a part of a nucleotide sequence encoding a ripening form of a polypeptide having sulfhydryl oxidase activity with an amino acid sequence as shown in FIG. 7 and even more concretely a recombinant DNA material comprising at least a part of the nucleotide sequence encoding a ripening form of a polypeptide with sulfhydryl oxidase activity as shown in FIG. 7. The genetic variants of the nucleotide sequence of FIG. 7, including sequences encoding mutant sulfhydryl oxidase polypeptides and degenerate nucleotide sequences coding for polypeptides wherein the sulfhydryl oxidase activity is retained are also part of the invention, as are nucleotide sequences capable of hybridizing to at least a part of the nucleotide sequences encoding a polypeptide having sulfhydryl oxidase activity as shown in FIG. 7 and genetic variants thereof (as described above), wherein said nucleotide sequences may differ in codon sequence due to the degeneracy of the genetic code or cross species variation. A polypeptide having sulfhydryl oxidase activity derived from Aspergillus niger was used to obtain the nucleotide sequence and amino acid sequence given in FIG. 7.

Figure 5C:
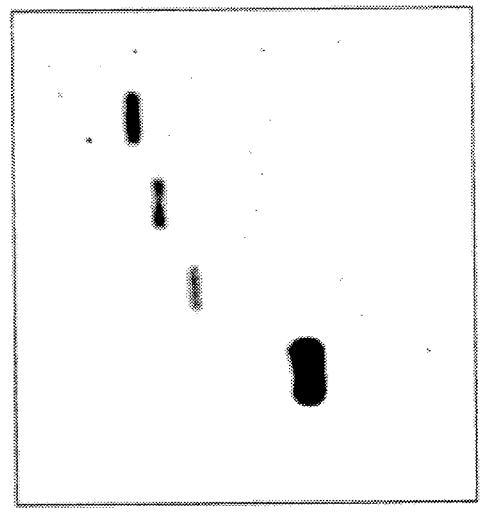
FIG. 5: Southern analysis of various strains of different species of filamentous fungi for the presence of genes closely related to the sox gene of *A. niger*.
Figure 5B:
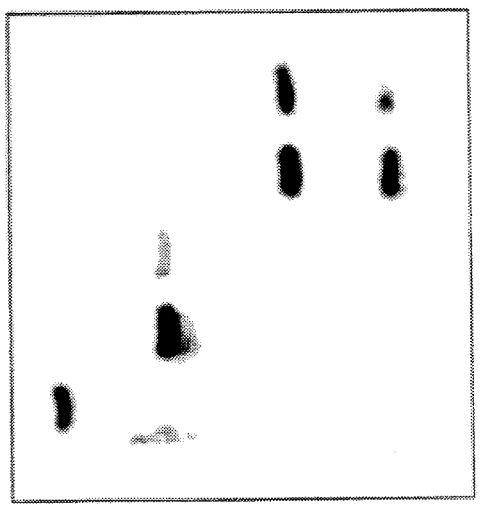
Figure 5A:
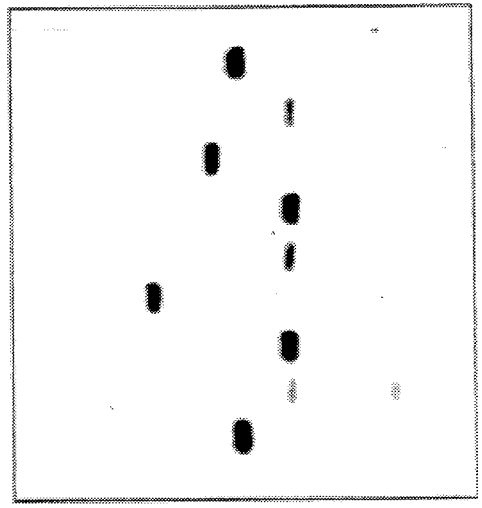

As is apparent from the analysis in FIG. 5 DNA sequences showing a great deal of homology with the Aspergillus sulfhydryl oxidase nucleotide sequence of FIG. 7 are present in other organisms. A part of the amino acid sequence of a ripening form of a polypeptide having sulfhydryl oxidase activity according to FIG. 7 therefore not only codes for a part of a polypeptide of *Aspergillus niger* origin having sulfhydryl oxidase activity but also codes for at least a part of a polypeptide having sulfhydryl oxidase activity that can be derived from a different organism.

Such a nucleotide sequence from another organism can be selected due to the fact that at least a part of the nucleotide sequence of FIG. 7 as derived from the *Aspergillus niger* N400 or a corresponding degenerate DNA sequence derived from the amino acid sequence of FIG. 7 or derived from an equivalent amino acid sequence can hybridize with genetic material of said other organism. The hybridizing part of the genetic material of the other organism comprises at least a part of a nucleotide sequence encoding a ripening form of a polypeptide having sulfhydryl oxidase activity. Using these sequences and the process for recovering such a nucleotide sequence as given in Example I, a person skilled in the art can derive a nucleotide sequence encoding a ripening form of a polypeptide having sulfhydryl oxidase activity from another organism.

The recombinant DNA material according to the invention can be used to express a nucleotide sequence encoding a ripening form of a polypeptide having sulfhydryl oxidase activity or the recombinant DNA material can be used as a probe or a primer for detection or production of genetic material encoding at least a part of a ripening form of a polypeptide with sulfhydryl oxidase activity.

The recombinant DNA material according to the invention can comprise regulatory regions native to the organism from which the nucleotide sequence encoding the polypeptide having sulfhydryl oxidase activity is derived operably linked to said nucleotide sequence. Said native regulatory regions can be the regulatory regions that regulate the sulfhydryl oxidase gene in the organism of origin of said polypeptide but can also be regulatory regions that regulate a different gene in said organism of origin. A regulatory region other than the native regulatory region that regulates the sulfhydryl oxidase gene in the organism of origin of said gene will generally be selected for its higher efficiency. It is also possible to select a regulatory region such as a promoter on the basis of other desirable characteristics, for example thermo inducibility. The selection of a desirable regulatory region will be obvious to one skilled in the art.

In another embodiment the recombinant DNA material according to the invention can comprise regulatory regions foreign to the organism from which the nucleotide sequence encoding the polypeptide having sulfhydryl oxidase activity is derived operably linked to said nucleotide sequence. In this instance the regulatory regions can be regulatory regions that regulate a sulfhydryl oxidase gene in the foreign organism from which they are derived or can be regulatory regions that regulate a gene other than the sulfhydryl oxidase gene in the foreign organism.

The selection of a desirable regulatory region will be obvious to one skilled in the art and will for example depend on the host cell into which the recombinant DNA material according to the invention is introduced. If a heterologous expression host is preferred, meaning that the nucleotide sequence encoding a polypeptide having sulfhydryl oxidase activity is derived from another strain of organism than the host cell (e.g. a different strain, variety, species, genus, family, order, class, division or kingdom) the regulatory region is preferably a regulatory region derived from an organism similar to or equal to the expression host. For example, if the nucleotide sequence is derived from a fungus and the expression host is a yeast cell, then the regulatory region will be derived from a yeast cell. The regulatory region need not however necessarily be derived from the same strain or the same genus as the host cell, i.c. a yeast cell. The selection of a yeast cell promoter in this instance is required to enable expression of the nucleotide sequence.

A regulatory region operably linked to a nucleotide sequence encoding a ripening form of a polypeptide having sulfhydryl oxidase activity in the recombinant DNA material according to the invention can be e.g. a constitutive promoter or an inducible promoter. Especially suited are constitutive promoters derived from genes encoding enzymes involved in the glycolytic pathway.

An example of a recombinant DNA material according to the invention comprising a strong constitutive promoter operably linked to the nucleotide sequence encoding a ripening form of sulfhydryl oxidase activity is a recombinant DNA material wherein said promoter is the glyceraldehyde-3-phosphate dehydrogenase (gpdA) promoter. This promoter is preferred for constitutive expression when recombinant DNA material according to the invention is expressed in a fungal expression host. Other examples are pgk, the phosphoglycerate kinase promoter, pki, the pyruvate kinase promoter, TPI, the triose phosphate isomerase promoter, the APC synthetase subunit g (oliC) promoter and the acetamidase (amdS) promoter.

Examples of recombinant DNA material according to the invention comprising inducible promoters operably linked to the nucleotide sequence encoding a ripening form of sulfhydryl oxidase activity are recombinant DNA materials, wherein said inducible promoters are selected from the promoters of the following genes: endoxylanase II A (exlA), glucoamylase A (glaA), cellobiohydrolase (cbh), amylase (amy), invertase (suc) and alcohol dehydrogenase alcA, TAKA amylase and amyloglucosidase (AGT). Preferably the inducible endoxylanase II A promoter is selected.

Examples of recombinant DNA material according to the invention comprising strong yeast promoters operably linked to the nucleotide sequence encoding a ripening form of sulfhydryl oxidase activity are recombinant DNA materials, wherein said yeast promoters are selected from the promoters of the following genes: alcohol dehydrogenase, lactase, 3-phosphoglycerate kinase, triose phosphate isomerase, α-D-galactose-phosphate uridyl transferase (Gal7) and glyceral-dehyde-3-phosphate dehydrogenase (GAPDH).

Examples of recombinant DNA material according to the invention comprising bacterial promoters operably linked to the nucleotide sequence encoding a ripening form of sulfhydryl oxidase activity are recombinant DNA materials, wherein said bacterial promoters are selected from the promoters of the following genes: α-amylase, SPO2 and extracellular proteases.

In the same manner that regulating regions foreign to the sulfhydryl oxidase gene can be coupled to said gene, it is also possible to couple a regulating region of a sulfhydryl oxidase gene to other genes. The invention is therefore also directed at a nucleotide sequence comprising at least a regulating region of a sulfhydryl oxidase enzyme and at use of such a nucleotide sequence e.g. for improved expression of a gene to which said sequence is coupled.

If a heterologous expression host is a yeast or a bacterial strain a recombinant DNA material according to the invention comprising an uninterrupted (intronless) nucleotide sequence encoding a ripening form of a polypeptide having sulfhydryl oxidase activity is preferred. This preference stems from the fact that the possibility that the heterologous host does not recognize splicing signals residing on the recombinant DNA material can thus be avoided. Such an uninterrupted nucleotide sequence may be obtained from a cDNA library constructed from RNA isolated from cells expressing a nucleotide sequence encoding a ripening form of a polypeptide with sulfhydryl oxidase activity. Alternatively an uninterrupted nucleotide sequence may be obtained by applying one or more polymerase chain reactions using suitable primers, so as to precisely remove the introns, using genomic DNA as a template, as is known to a person skilled in the art.

For the expression in yeast such as *Saccharomyces cerevisiae* it is preferable that the introns are removed and that the fungal SOX leader sequence is replaced by a signal sequence suitable for yeast such as the signal sequence of the invertase gene ensuring correct processing and secretion of the mature polypeptide.

The removal of introns is necessary for expression in bacteria such as *Bacillus subtilis*. In this case for example the α-amylase signal sequence can be used as signal sequence.

A preferred embodiment of recombinant DNA material according to the invention comprises a selection marker. Such a selection marker serves to discriminate host cells into which the recombinant DNA material has been introduced from cells that do not comprise said recombinant DNA material. This selection marker provided with the appropriate regulatory sequences may reside on the same DNA fragment containing the nucleotide sequence encoding a ripening form of a polypeptide having sulfhydryl oxidase activity or can be present on a separate fragment. In the latter case a co-transformation must be performed with the various components of the recombinant DNA material according to the invention. The ratio of expression component (containing the nucleotide sequence encoding a ripening form of a polypeptide having sulfhydryl oxidase activity) / selection component (with the selection marker) can be adjusted in such a manner that a high percentage of the selected cells comprising the selection component have also incorporated the expression component. The term recombinant DNA material as used herein therefore comprises one or more recombinant DNA fragments, wherein the selection marker can be incorporated on the same recombinant DNA molecule as the nucleotide sequence encoding a ripening form of a polypeptide having sulfhydryl oxidase activity or on a different recombinant DNA fragment.

Very often filamentous fungi are transformed through co-transformation. For example a pyrA⁻ strain (pyrA=orotidine-5'-phosphate decarboxylase) can be used as host cell and the recombinant DNA material according to the invention will comprise a DNA molecule comprising the nucleotide sequence encoding a ripening form of a polypeptide having sulfhydryl oxidase activity and another DNA molecule comprising the pyrA gene. After transformation of the pyrA⁻ strain any resulting pyrA⁺ strain will obviously have incorporated some recombinant DNA material and will most probably also comprise the nucleotide sequence encoding a ripening form of a polypeptide having sulfhydryl oxidase activity. Very often such co-transformation will lead to incorporation of the component of recombinant DNA material according to the invention comprising the nucleotide sequence encoding a ripening form of a polypeptide having sulfhydryl oxidase activity per host cell in multiple copies (multicopy incorporation). This is a well-known route for producing multicopy tranformants in general.

Other well-known selection systems for industrial microorganisms are those formed by the group of selection markers which do not require a mutation in the host organism. Examples of fungal selection markers are the genes for acetamidase (amdS), ATP-synthetase, subunit 9 (oliC) and benomyl resistance (benA). Another example of a fungal selection marker is the nitrate reductase system. Exemplary of non-fungal selection markers are the g418 resistance gene (yeast), the ampicillin resistance gene (*E. coli*) and the neomycin resistance gene (Bacillus), a gene conferring resistance to hygromycin (hph) or a gene conferring resistance to fleomycin (Ble).

Suitable transformation methods and suitable expression vectors provided with e.g. a suitable transcription promoter, suitable transcription termination signals and suitable marker genes for selecting transformed cells are already known for many organisms including different bacterial, yeast, fungal and plant species. Reference may be made for yeast for example to Tagima et al. Yeast 1, 67–77, 1985, which shows expression of a foreign gene under control of the gal7 promoter inducible by galactose in yeast and for *Bacillus subtilis* for example in EP-A-0,157,441 describing a plasmid pNS48 containing the SPO2 promoter as an expression vector. For the possibilities in these and other organisms reference is made to the general literature.

Overexpression of a ripening form of a polypeptide having sulfhydryl oxidase activity may be achieved by the incorporation of recombinant DNA material according to the invention in an expression host, said recombinant DNA material comprising one or more regulatory regions (selected for example from promoter and terminator regions) which serve to increase expression levels of the polypeptide of interest from said expression host. If desired the polypeptide of interest can be secreted from the expression host. This can be achieved by incorporating recombinant DNA material according to the invention as described further comprising at least one signal sequence (e.g. a pre or prepro sequence).

The present invention is not only directed at the recombinant DNA material comprising at least a part of a nucleotide sequence encoding a ripening form of a polypeptide having sulfhydryl oxidase activity in the various embodiments as described above but is also directed at a cell comprising at least a part of said recombinant DNA material, said cell being capable of expression of said nucleotide sequence.

Progeny of an expression host comprising recombinant DNA material according to the invention is also embraced by the present invention.

Preferably a cell according to the invention will be capable of overexpression of a nucleotide sequence encoding a ripening form of a polypeptide having sulfhydryl oxidase activity. Within the context of the present invention overexpression is defined as the expression of the ripening form of a polypeptide having sulfhydryl oxidase activity at levels above those ordinarily encountered under the same conditions in the native organism from which said polypeptide originates. In the same context overexpression also covers the expression of the ripening form of a polypeptide having sulfhydryl oxidase activity in an organism other than the organism from which the nucleotide sequence comprised on the recombinant DNA material according to the invention can be derived, a so called heterologous organism. The heterologous host organism does not normally produce such a ripening form of a polypeptide having sulfhydryl oxidase activity at appreciable levels and the heterologous organism is therefore only capable of such production after introduction of the recombinant DNA material according to the invention.

As already stated, overexpression of a ripening form of a polypeptide having sulfhydryl oxidase activity may be achieved by incorporation of recombinant DNA material according to the invention.

In order to obtain overexpression recombinant DNA material according to the invention can be incorporated in a homologous expression host. The term "homologous expression host" means that the non transformed expression host belongs to the same strain or species as the organism from which the nucleotide sequence encoding a ripening form of a polypeptide having sulfhydryl oxidase activity that is comprised on the recombinant DNA material according to the invention has been derived.

Introduction of the recombinant DNA material according to the invention into a homologous expression host will result in the expression host comprising at least two nucleotide sequences encoding a ripening form of polypeptide having sulfhydryl oxidase activity, becoming a so-called multicopy transformant.

The overexpression can be further achieved by the introduction of the recombinant DNA material according to the invention into a host belonging to a strain other than the strain from which the nucleotide sequence encoding a ripening form of polypeptide having sulfhydryl oxidase activity was isolated a so-called heterologous host, such that the resulting expression host comprises a nucleotide sequence encoding a ripening form of polypeptide having sulfhydryl oxidase activity in increased gene copy numbers, becoming a so-called multicopy transformant.

The methods generally known for obtaining multicopy transformants can be used. The recombinant DNA material according to the invention therefore comprises any embodiment required for obtaining a multicopy transformant comprising multiple copies of the nucleotide sequence encoding a ripening form of polypeptide having sulfhydryl oxidase activity.

The overexpression can also be achieved by the introduction of the recombinant DNA material according to the invention in the various embodiments already described into a host cell such that the host cell comprises the nucleotide sequence encoding a ripening form of polypeptide having sulfhydryl oxidase activity under the control of a regulatory region other than the native regulatory region for the sulfhydryl oxidase gene in the organism from which said nucleotide sequence is derived, said other regulatory region preferably being more efficient than the native regulatory region. The invention is also directed at recombinant DNA material in any of the various embodiments described further comprising a regulatory region other than the native regulatory region for the sulfhydryl oxidase gene in the organism from which said nucleotide sequence is derived. Such a host cell can be either homologous or heterologous. The host cell can comprise one or more copies of the nucleotide sequence encoding a ripening form of polypeptide having sulfhydryl oxidase activity comprised on the recombinant DNA material according to the invention.

In some instances it can be preferable to introduce recombinant DNA material according to the invention in such a manner that said recombinant DNA material is integrated in the chromosomal DNA of the host cell. In fungal cells chromosomal integration always takes place in successful transformations. No plasmid DNA is maintained. In yeast both plasmids and integrated DNA can be maintained satisfactorily.

It is possible to introduce recombinant DNA material into the host cell such that the genetic properties that are introduced are located on extra-chromosomal DNA most often called "plasmids". Plasmids have the advantage that they exist normally in the cell in multiple copies which also means that a certain gene located on such a plasmid exists in the cell in multicopy form which may result in a higher expression of the proteins encoded by the genes. However, the disadvantage of plasmids is that they can be unstable resulting in a possible loss of the plasmids from the cells at a certain stage. The loss of a plasmid can be prevented by using a plasmid comprising at least one stretch of nucleotides capable of hybridizing with chromosomal DNA of the non-transformed host cell enabling said vector to integrate stably into the chromosome of said host cell after transformation. Use of a stretch of homologous DNA that is already present in multiple copies in the chromosomal DNA will lead to multicopy insertion of the vector DNA resulting in integrated multimeric DNA comprising one or more copies of the nucleotide sequence encoding a ripening form of a polypeptide having sufhydryl oxidase activity. Another prerequisit for a vector resulting in integrated DNA in the chromosomal DNA is that the vector does not comprise a functional replicon as the vector must be unable to maintain itself in the host cell unless it is integrated.

The stretch of nucleotides enabling integration is preferably derivable from DNA that comprises at least part of a non-essential portion of the chromosome of a non-transformed host cell (in this instance the term "derivable from" implies that the stretch of nucleotides in the vector according to the invention must show enough homology with the chromosomal DNA to enable hybridization for an integration event to occur). The integration of the vector will subsequently take place in said non-essential portion of the chromosome of the host cell and will not lead to the loss of essential function of the host cell. It is preferable for the integration to take place in a non-essential selectable gene of the chromosome of the non-transformed host cell. This can be subsequently a selection criterium for transformed host cells.

In the case of fungal cells it is only possible to successfully obtain transformants having DNA integrated in the chromosomal fungal DNA as plasmids cannot be maintained in such cells. In fungal cells it is not even necessary to include homologous chromosomal DNA as multicopy integration takes place without said homologous DNA. In the case of yeast cells it is optional to have the desired DNA in the transformant either as a plasmid or as integrated DNA. For integration in yeast cells DNA sequences homologous to chromosomal DNA must be present.

A preferred embodiment of the invention is directed at a cell comprising recombinant DNA material according to the invention in any of the embodiments described, wherein said cell is capable of secreting a ripening form in particular capable of secreting a mature form of a polypeptide with sulfhydryl oxidase activity as encoded by said recombinant DNA material. It is often desirable for the ripening form of a polypeptide having sulfhydryl oxidase activity to be secreted from the expression host into the culture medium as said polypeptide may be more easily recovered from the medium than from the cell. Preferably the mature form of the sulfhydryl oxidase will be secreted into the culture medium.

The term "secretion" in the subject invention comprises the polypeptide crossing a cell wall or a cell membrane. The polypeptide can pass such a cell wall or membrane into the culture medium but can also remain attached to said cell wall or cell membrane. The polypeptide can also pass a cell membrane into the periplasmic space and not into the culture medium. The processing c.q. secretion route to be followed by the ripening form of a polypeptide having sulfhydryl oxidase activity will depend on the selected host cell and the composition of the recombinant DNA material according to the invention. Most preferably, however, the polypeptide will be secreted into the culture medium.

The cell according to the invention can comprise recombinant DNA material in any of the various embodiments described further comprising DNA encoding the native leader sequence (pre or prepro) of the polypeptide having sulfhydryl oxidase activity. In another embodiment the cell according to the invention can comprise recombinant DNA material further comprising DNA encoding for foreign leader sequences (pre or prepro) instead of the native leader sequences. The invention is also directed at recombinant DNA material comprising DNA encoding the mature polypeptide having sulfhydryl oxidase activity coupled to DNA encoding a leader sequence foreign to the polypeptide having sulfhydryl oxidase activity.

An increase in the expression of a polypeptide having sulfhydryl oxidase activity can result in the production of polypeptide levels beyond those the expression host is capable of processing and secreting resulting in a build up of polypeptide product within the host cell creating a bottle neck in the transport of the polypeptide through the cell membrane or cell wall. Accordingly the present invention is also directed at a cell comprising recombinant DNA material in any of the various embodiments described comprising heterologous signal sequences to provide for the most efficient secretion of the sulfhydryl oxidase from the chosen expression host and the invention is also directed at said recombinant DNA material.

A heterologous secretion signal sequence may be chosen such that it is derived from the same strain as the organism from which the other regulatory regions of the nucleotide sequence encoding a ripening form of a polypeptide having sulfhydryl oxidase activity have been derived, preferably from the same gene. For example the signal of the highly secreted amyloglucosidase protein may be used in combination with the amyloglucosidase promoter itself as well as in combination with other promoters.

Examples of preferred heterologous secretion signal sequences are those originating from the glucoamylase A or endoxylanase II A gene for fungi, the invertase gene for yeast and the α-amylase gene for Bacillus.

Hybrid secretion sequences may also advantageously be used within the context of the present invention.

In general terminators of transcription are not considered to be critical elements for the overexpression of genes. If desired, a terminator of transcription may be selected from the same gene as the promoter or alternatively the homologous terminator may be employed. In fact any terminator can be employed.

Factors such as size (molecular weight) the possible need for glycosylation or the desirability of the secretion over the cell membrane or cell wall or into the medium of the sulfhydryl oxidase play an important role in the selection of the expression host.

Partly depending on the selected host cell the nucleotide sequence encoding a polypeptide having sulfhydryl oxidase activity will be used either with or without introns occurring in said DNA sequence either with its own promoter and/or transcription termination signals or originating from another gene and either with its own leader sequence or with a signal sequence originating from another gene.

In principle the invention knows no special limitations with respect to the nature of the cells comprising recombinant DNA material according to the invention. Cells according to the invention may be important as agents for multiplying the recombinant DNA material or as agents for producing a ripening form of a polypeptide having sulfhydryl oxidase activity.

Those expression hosts capable of overexpression of a nucleotide sequence encoding a ripening form of a polypeptide having sulfhydryl oxidase activity are preferred. In particular an expression host cell capable of secretion of a ripening form of polypeptide having sulfhydryl oxidase activity is preferred.

The expression hosts are preferably selected from the group consisting of bacterial cells, fungal cells, yeast cells and plant cells.

Preferred examples of eminently suited host cells are a) fungal cells, in particular filamentous fungal cells, such as a fungal cell from the group comprising the genera Aspergillus, Trichoderma, Neurospora, Penicillium and Mucor. Examples of particular species that are suitable as host cell are fungal cells of one of the species *Aspergillus niger, Aspergillus awamori, Aspergillus oryzae, Aspergillus sojae, Aspergillus tubigensis, Aspergillus aculeatus, Aspergillus japonicus, Trichoderma reesei* and *Trichoderma viride;* b) yeast cells, for example of the genera Saccharomyces, Kluyveromyces, Hansenula and Pichia, in particular yeast cells of one of the species *Saccharomyces cerevisiae, Saccharomyces carlbergensis, Kluyveromyces lactis, Kluyveromyces marxianus, Hansenula polymorpha* and *pichia pastoris;* c) plant cells of a plant genus selected for example from the group consisting of wheat, barley, oats, maize, pea, potato and tobacco such as plant cells of one of the species *Solanum tuberosum* and *Nicotiana tobaccum;* and d) bacterial cells, preferably gram positive bacterial cells, for example of one of the bacterial genera Bacillus, Lactobacillus and Streptococcus such as bacteria of the species *Bacillus subtilis* or *Bacillus licheniformis.*

The host cell to be selected for recombinant DNA material according to the invention will amongst others depend on the application for which the resulting polypeptide having sulfhydryl oxidase activity is destined.

A preferred cell according to the invention is a foodgrade cell. This preference stems from the fact that products of such foodgrade cells can be used in processes for producing foodstuffs. Bacteria from the genus Bacillus are very suitable as expression host cells because of their capability to secrete proteins into the culture medium. Alternatively a host selected from the group of yeasts or fungi may be preferred. In some instances yeast cells are easier to manipulate than fungal cells. However, some proteins are either poorly secreted from the yeast cell or in some cases are not processed properly (e.g. hyper-glycosylation in yeast). In these and other instances a fungal host organism can be selected. A fungal host is often suitable if it has GRAS status (GRAS=generally regarded as safe). In general, eukaryotic hosts have been found to have a high productivity of secreted active polypeptides. In fact fungal hosts are very often used in industrial processes, particularly suitable examples of a host cell are therefore *Aspergillus niger* and *Aspergillus niger* var. awamori. These particular species of Aspergillus have previously been demonstrated to be excellent host cells for industrially producing enzymes. A person skilled in the art is able to obtain multicopy transformants of these species.

In the case of polypeptide production it is possible to use the expression host cell to produce polypeptide and to subsequently either isolate the polypeptide from the culture medium or use the medium containing the polypeptide as such after removal of the cells. It is even possible to use the cells themselves to produce the polypeptide in situ in the process for which the polypeptide having sulfhydryl oxidase activity is required. In the preparation of foodstuffs such a host strain that is to be used directly can only be used if it is a food grade host strain. In connection with bread making for example yeast strains that have been genetically manipulated in accordance with the present invention can be used directly.

If the polypeptide is required in extremely purified forms or if particular contaminants are deleterious to the application of the resulting polypeptide, the expression host cell can be selected to avoid such problems. For example the presence of glucose oxidase as contaminant of the polypeptide having sulfhydryl oxidase activity can be elminated if a host cell that is glucose oxidase negative is selected. It is known that many microorganisms that naturally produce SOX also produce glucose oxidase in a lot larger amounts than SOX. In a cell according to the invention SOX can be overexpressed, however, this does not necessarily mean that the amount of SOX will be equal to or larger than the amount of GOX produced. In order to prevent contamination of SOX with GOX and in order to eliminate the necessity of purifying SOX from GOX, a host cell that is GOX⁻ can be used to express the recombinant DNA comprising a nucleotide sequence encoding a ripening form of a polypeptide having sulfhydryl oxidase activity. Such a host cell could for example be a strain derived from *Aspergillus niger* N400 (CBS 120.49) or *Aspergillus niger* var. awamori (CBS 115.52).

A similar reasoning can be used when SOX is to be applied for removing off flavour in UHT treated milk. In this instance the presence of protease as contaminant is not desirable. Presence of protease, in particular, should be avoided when long term storage is being contemplated for SOX-treated UHT milk. It is possible to use size exclusion chromatography involving BioGel P100 (BioRad) to effectively reduce the content of undesirable proteases by 80–90%. In addition to size exclusion chromatography, protease activity can be removed by other well-known techniques such as ion exchange chromatography, bentonite treatment, or pH/temperature inactivation. In order to avoid such costly and complicated steps it is however preferable to select a prt⁻ strain as host cell.

The subject invention is also directed at a ripening form of a polypeptide with sulfhydryl oxidase activity wherein said ripening form is obtainable by expression of the recombinant DNA material according to the invention. Preferably a polypeptide with sulfhydryl oxidase activity of microbial origin is claimed as this is known to be effective in both removal of off-flavour from UHT milk and in improving bakery products. In particular a microorganism belonging to the genus Aspergillus is a preferred source of a ripening form of a polypeptide with sulfhydryl oxidase activity according to the invention. The invention is preferably directed at a mature form of a polypeptide with sulfhydryl oxidase activity as no further treatment of said polypeptide is necessary before using said polypeptide in a desired process. In particular the invention is directed at a ripening form of a polypeptide as encoded by a part of the DNA sequence of FIG. 7. A ripening form of a polypeptide having sulfhydryl oxidase activity, said ripening form being encoded by a part of a DNA sequence encoding a polypeptide with an equivalent tertiary structure having sulfhydryl oxidase activity also forms part of the invention.

The invention is also directed at a process for producing a ripening form of a polypeptide having sulfhydryl oxidase activity comprising the culture of a cell as previously described in the specification and optionally isolation of the resulting ripening form of a polypeptide having sulfhydryl oxidase activity. The expression of the polypeptide with sulfhydryl oxidase activity can be effected by culturing expression host cells that have been transformed with the recombinant DNA material comprising a nucleotide sequence encoding a ripening form of a polypeptide having sulfhydryl oxidase activity in a conventional nutrient fermentation medium.

The fermentation medium can comprise an ordinary culture medium containing a carbon source, a nitrogen source, an organic nitrogen source and inorganic nutrient sources. The selection of the appropriate medium may be based on the choice of expression host and/or based on the regulatory requirements of the recombinant DNA material. Such media are well-known to those skilled in the art. The medium may, if desired, contain additional components favouring the transformed expression host over other potentially contaminating microorganisms. In the case of production of the polypeptide having sulfhydryl oxidase activity for food processing such additional components are necessarily also food grade.

After fermentation the cells can be removed from the fermentation broth by means of centrifugation or filtration. Depending on whether the host cell has secreted the polypeptide having sulfhydryl oxidase activity into the medium or whether said polypeptide is still connected to the host cell in some way either in the cytoplasm, in the periplasmic space or attached to or in the membrane or cell wall, the cells can undergo further treatment to obtain the polypeptide.

In the latter case, where the polypeptide is still connected to the cell in some manner, recovery of the polypeptide can for example be accomplished as described in U.S. Pat. No. 4,894,340 or U.S. Pat. No. 4,632,905 by rupturing the cells for example by high pressure disruption, sonication, enzymatic digestion or simply by cell autolysis followed by subsequent isolation of the desired product. The polypeptide can be separated from the cell mass by various means. In one such method the cells are disrupted by the protease ficin and subjected to ultrafiltration. The polypeptide is subsequently precipitated with an organic solvent such as methanol or acetone. The polypeptide can also be separated from the cell mass by suspending the microorganism in a brine solution sufficient to partition the polypeptide into the brine solution (for example 20% (w/v) NaCl). It is suggested that the brine solution creates osmotic pressure sufficient enough to partition a polypeptide into the brine solution. In general the same methods heretofore employed to liberate and produce solutions of other intracellular enzymes can be employed.

The polypeptide isolated from microbial cells is generally purified by conventional precipitation and chromatographic methods. Such methods include amongst others methanol, ethanol, acetone and ammonium sulfate precipitation and ion exchange and hydroxy apatite chromatography. In particular acetone precipitation and hydroxy apatite chromatography effectively purify the polypeptide by taking advantage of the unusual solubility and stability of the polypeptide in water acetone mixtures as compared with other protein constituents of the extract.

The use of a cell as described herein or a ripening form of a polypeptide having sulfhydryl oxidase activity of microbial origin according to the invention in a process requiring oxidation of free sulfhydryl groups to disulfide linkages also producing $H_2O_2$ are also a part of the invention. This use may be directed to a process for improving characteristics of dough in particular in a process for improving the characteristics of (frozen) dough or to a process for removing off flavour from foodstuffs such as dairy products (that have been subjected to UHT sterilisation) and beer.

Thus, a composition such as a bread improver, a dough improver or a flour comprising a ripening form of a polypeptide with sulfhydryl oxidase activity according to the invention or a ripening form of a polypeptide with sulfhydryl oxidase activity that can either be obtained from a cell or through the process as described herein or such cells themselves are also a part of the invention. A process for preparing a bakery product which comprises using such a composition are also a part of the invention.

A ripening form of a polypeptide with sulfhydryl oxidase activity as described herein or a ripening form of a polypeptide with sulfhydryl oxidase activity that can either be obtained from a cell or through the process of as described herein may also be applied to a composition for use in a personal product. Such a composition may be used for reinforcing the structure of proteins or proteinaceous structures or may be used in a composition suitable for scavenging off flavours or smells.

The use of a part of recombinant DNA material as described herein comprising a part of a nucleotide sequence encoding a ripening form of a polypeptide having sulfhydryl oxidase activity as a probe or a primer for detection, isolation or production of a nucleotide sequence encoding a polypeptide with sulfhydryl oxidase activity is also a part of the invention.

Example I

Cloning and characterization of the sulfhydryl oxidase (sox) gene of *Aspergillus niger*

1.1: Establishing the N-terminal (SEQ ID NO: 3) amino acid sequence of the *A. niger* SOX protein 1.1.1 Isolation of SOX from commercial GOX preparations Sox protein was purified from a commercial preparation of glucose oxidase (GOX) obtained from Finnsugar Bioproducts (product P110, Glucose oxidase LC5000), derived from *Aspergillus niger*.

Fractionation was performed essentially as described by De la Motte and Wagner (1987), using standard protein purification techniques such as selective precipitation with acetone, different types of ion-exchange chromatography, hydrophobic interaction chromatography and gel filtration chromatography. Fractions enriched in oxidase activity were identified using an assay described in the literature (De la Motte and Wagner, 1987). Fractions enriched in SOX protein were further purified by standard methods until a single band resulted upon SDS-PAGE. Enzymatic activity, pH-optimum and other characteristics of the purified enzyme correspond to those reported for Aspergillus niger SOX (De la Motte and Wagner, 1987).

1.1.2 Determination of the N-terminal (SEQ ID NO: 3) amino acid sequence of *Aspergillus niger* SOX The purified SOX fraction was used for determination of the N-terminal (SEQ ID NO: 3) amino acid sequence of *A. niger* SOX using the sequential degradation method of Edman, and an Applied Biosystems Sequencer Model 475 with an on-line PTH-analyzer model 120A. (FIG. 1, sequence listing no. 3).

1.1.3 Determination of amino acid sequences of internal regions of *A. niger* SOX The purified SOX fraction was used to generate fragments of the SOX polypeptide by cleavage with CNBr according to Gross and Witkop (described in "Sequencing of Proteins and Peptides", G. Allen, Laboratory Techniques in Biochemistry and Molecular Biology, Ed. T. S. Work and R. H. Burdon, 1981). The fragments were separated by HPLC, using a Bakerbond C4 wide pore column (5 μm; 4.6*250 mm) (FIG. 2A). The fraction corresponding to peak 9 in FIG. 2A was named CNBr fragment #9 (SEQ ID NO: 4), and was subjected to amino acid sequence analysis according to the method of Edman (FIG. 2B, sequence listing no. 4).

1.2: Identification of strains of filamentous fungi secreting SOX

Various strains of different species of filamentous fungi were cultured under standardized conditions in order to compare their natural production levels of SOX activity under these conditions. Fermentations were performed in a Chemoferm glass 10 liter fermentor, equiped with a magnetically driven eight blade impeller. The dissolved oxygen tension was measured with an Ingold oxygen probe, the pH was determined with an Ingold pH electrode, and the temperature was measured using a PT100 sensor. The working volume of the fermentor was 8 liter, containing a medium of the following composition (per liter): 20 g sucrose, 12 g $NaNO_3$, 5 g $K_2HPO_4$, 2 g $MgSO_4 \cdot 7H_2O$, 0.5g yeast extract and 20 ml of a trace elements solution (Visniac, 1957). Applikon ADI 1020 control units were used for control of pH, temperature, $pO_2$ and gass inlet (1.5 l/min air and 1.5 l/min oxygen) and stirrer speed (600–1000 rpm). During the fermentation the pH was kept at 5.5 by the addition of 12.5% $NH_4OH$, the temperature was kept at 30° C. and the $pO_2$ at 30% or higher by manual adjustment of the stirrer speed. Fermentors were inoculated with precultures (5%). Precultures (two 500 ml conical, baffled shakeflasks containing 200 ml fermentation medium each) were inoculated with fungal spores ($10^6$–$10^7$ spores/ml) and incubated overnight at 25° C. and 250 rpm in a shaking incubator. The fermentation process was carried out for 80 hr or longer, followed by isolation of SOX, essentially as described by De la Motte and Wagner (1987). With the exception of the tested *Aspergillus oryzae* and *Penicillium linalicum* strains, most strains of filamentous fungi proved to be capable of production of SOX activity, implying that these organisms contain a gene encoding a protein with SOX activity, and therefore can be used to isolate such a gene and, in principle, can be used for the overproduction of proteins with SOX activity. The absolute amount of SOX protein produced under these conditions was rather low (FIG. 3), and was not produced until the onset of the growth cessation/decelleration phase. In most cases the SOX activity was found to be predominantly associated with the fungal cells, the single exception being *Aspergillus niger* strain N400. Therefore, DNA isolated from this strain was used as starting material for the isolation of the *Aspergillus niger* sox gene.

1.3: Cloning the sox gene of *Aspergillus niger*

All techniques used for the manipulation and analysis of nucleic acid materials were performed essentially as described in Maniatis et al. (1982), except where indicated otherwise.

1.3.1 Isolation of a DNA fragment containing part of the SOX gene of *Aspergillus niger*

Figure 2:
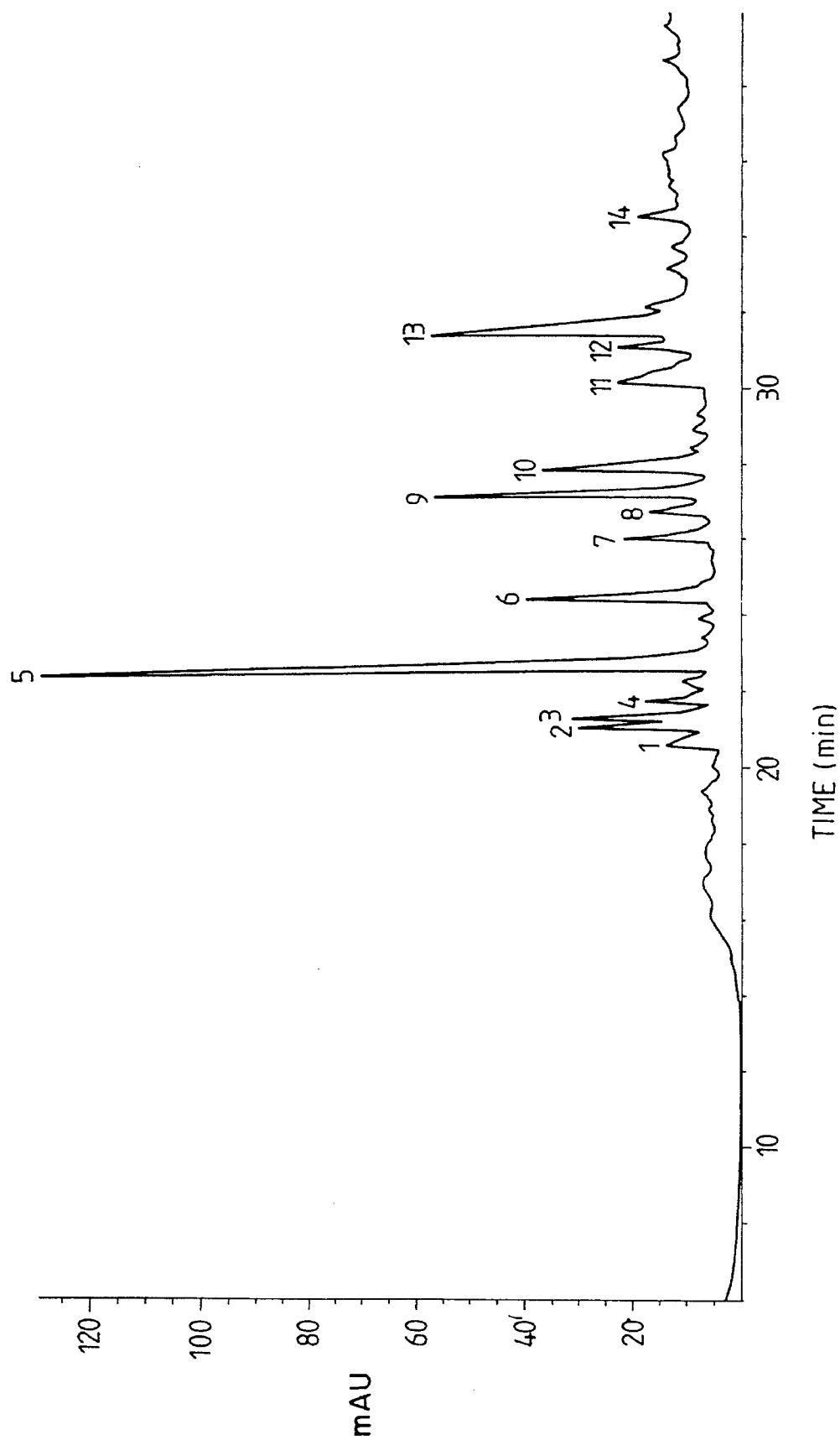
FIG. 2A: Elution profile of HPLC separation of SOX CNBr fragments
FIG. 2B: Partial amino acid sequence of fragment of *Aspergillus niger* sulfhydryl oxidase generated by cleavage with cyanogen bromide and sequence of derived degenerate mixtures of synthetic oligonucleotides.

The identified amino acid sequence of the N-terminus of *Aspergillus niger* SOX was used to derive a degenerate mixture of synthetic DNA oligonucleotides, comprising oligonucleotides capable of hybridizing to the coding strand of the sox gene of Aspergillus niger (FIG. 1). The identified amino acid sequence of the CNBr fragment#9 of *Aspergillus niger* SOX was used to derive degenerate mixtures of synthetic DNA oligonucleotides, which comprise oligonucleotides capable of hybridizing to the non-coding strand of the sox gene of Aspergillus niger (FIG. 2, sequence listing no. 5 and 6). These oligonucleotide mixtures were used as primers in PCR (polymerase chain reaction) amplification reactions using 100 pmol oligonucleotides of one of the mixtures derived from the N-terminal (SEQ ID NO: 3) amino acid sequence and 100 pmol of one of the mixtures derived from the amino acid sequence of CNBr fragment#9. The reactions were performed in the presence of 200 μM each of dATP, dCTP, dTTP and dGTP, 2.5 units Taq DNA polymerase (Boehringer Mannheim), 10 mM Tris/HCl (pH 8.3), 1.5 mM $MgCl_2$, 50 mM KCl and 0.1 mg/ml gelatin in a total volume of 100 μg using 1 μg genomic DNA of either *Aspergillus niger* N400 (CBS 120.49) or *Aspergillus tubigensis* CBS 115.29 as a template, which were isolated as described by De Graaff et al. (1988). Reaction mixtures were incubated in a Perkin-Elmer Cetus Thermal Cycler according to a program of 20 thermal cycles, (one cycle being: 1 min. at 95° C., 1 min. at 48° C. and 2 min. at 72° C.), preceeded by 4 min. at 95° C. and concluded with an incubation at 72° C. for 5 min. Gel electrophoretic analysis of the reaction products on agarose gels revealed that a DNA fragment of approximately 950 bp was selectively amplified when using mixtures SOX04WM (SEQ ID NO: 10) and SOX06WM (SEQ ID No: 12) as primers, both when using *Aspergillus niger* N400 or *Aspergillus tubigensis* CBS115.29 genomic DNA as a template. Southern hybridization analysis of restriction enzyme digests of the 950 bp PCR fragment generated with *Aspergillus niger* N400 DNA, using SOX05WM (SEQ ID NO: 11) as a probe, confirmed that the PCR fragment comprises part of the *Aspergillus niger* sox gene and allowed the mapping of KpnI and SalI restriction sites within the PCR fragment.

1.3.2 Northern analysis of sox mRNA in *Aspergillus niger*

Figure 4:
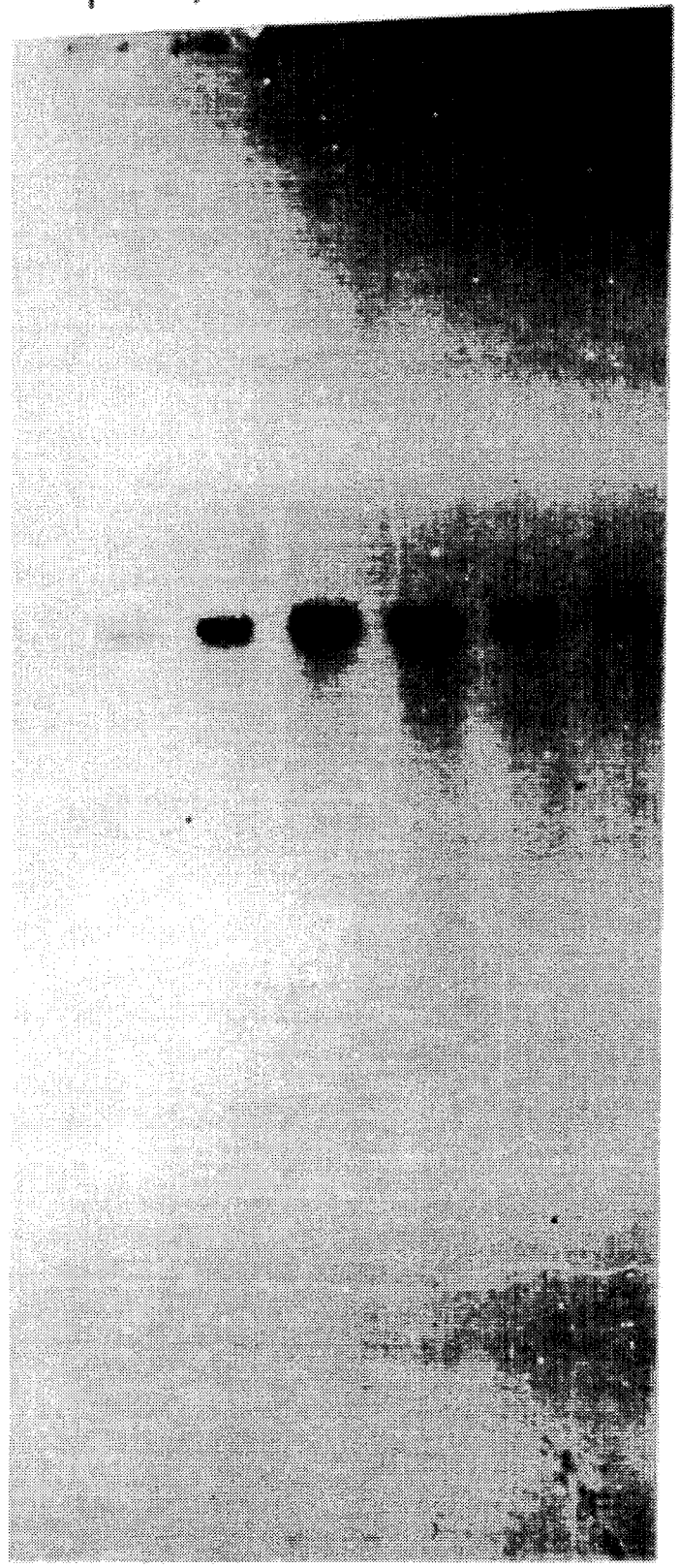
FIG. 4: Northern analysis of *A. niger* NW101 total RNA isolated after the indicated number of hours of fermentation for the presence sox mRNA.

*Aspergillus niger* NW101, a cspA1, goxC17, pabA1 derivative of *Aspergillus niger* N400 (Witteveen et al., 1990), was grown in a standard type 2 liter fermentor using a culture broth containing per liter (½ PM medium): 20 g fructose, 0.6 g $NaNO_3$, 0.25 g $KH_2PO_4$, 0.1 g $MgSO_4 \cdot 7H_2O$, 0.5 g yeast extract, 20 ml of a trace elements solution (Visniac, 1957) and 1.4 mg para-aminobenzoic acid. During the fermentation the pH was kept at 5.5 by the addition of 5M NaOH, the temperature was kept at 30° C. The $pO_2$ was kept above 30% by switching gass inlet from air to oxygen when neccesary. A fermentor containing 1.5 liters of fermentation medium was inoculated with a preculture (20%) of fungal spores. The preculture (a 1000 ml conical, baffled shakeflask containing 300 ml fermentation medium) was inoculated with 108 fungal spores and incubated for 6 hours at 30° C. and 250 rpm in a shaking incubator. The fermentation process was carried out for more than 80 hrs. Mycelium samples were taken after 24, 30, 47, 55, 71 and 81 hrs of cultivation. The stationary / decelleration phase of growth had been reached around 50 hrs after innoculation of the fermentor. Total RNA was prepared from each sample using the guanidinium thiocyanate method, essentially as described by Maniatis et al. (1982). For each time point 5 μg of total RNA was glyoxylated and subjected to Northern analysis for the presence of sox mRNA using the 950 bp PCR fragment as a probe (FIG. 4). For each sample only a single hybridization signal was detected at a position corresponding to a length of approximately 1500 nucleotides. The intensity of this signal gradually increases going from 24 hrs to 55 hrs after inoculation of the fermentor, reaches a maximum at 55 hrs and than gradually declines. Consequently, it can be concluded that the sox mRNA is about 1500 nucleotides in length, and that it is present in cells at late stages of growth.

1.3.3 Number of sox and closely related genes in *Aspergillus niger* and other filamentous fungi The PCR fragment of the *Aspergillus niger* sox gene was used as a probe in a Southern hybridization analysis to establish the number of sox (or closely related) genes that are present in the genome of *Aspergillus niger*, as well as the incidence of highly homologous genes in other species of Aspergilli. Using standard methods and conditions for heterologous hybridization and washing of the blot, the hybridization pattern of various restriction enzyme digests of *Aspergillus niger* genomic DNA revealed (FIG. 5) that the *Aspergillus niger* N400 (CBS 120.49) genome comprises only a single copy of the sox gene. Moreover, in the genomes of *Aspergillus niger* var. awamori (CBS 115.52), *Aspergillus sojae* (ATCC 20235), *Aspergillus tubigensis* (CBS 115.29) and *Aspergillus nidulans* WG096 (Glasgow strain FGSC 4, Barratt et al., 1965) the presence of at least a single gene which is highly homologous to the *Aspergillus Niger* sox gene, could be demonstrated. This result demonstrates that, now that the nucleotide sequence of the *Aspergillus niger* sox gene has been disclosed in this document (FIG. 7), the isolation of genes closely related to the *Aspergillus niger* sox gene from other filamentous fungi is an obvious procedure for a person skilled in the art, using the procedure outlined in this example.

1.3.4 Isolation of λ-clones comprising the *A. niger* sox gene

A library of *Aspergillus niger* N400 genomic DNA in λ-EMBL4 (Harmsen et al., 1990) was screened using the PCR fragment of the *Aspergillus niger* sox gene as a probe, which was labelled according to a standard random primer labeling protocol. Approximately $24*10^3$ plaques were tested in duplo (duplicate filters from each plate) according to standard methods (Maniatis et al., 1982) using *E. coli* LE392 as plating bacteria. The total length of the inserts contained within the analyzed plaques is equivalent to about 12 times the size of the *Aspergillus niger* genome. Hybridization was performed in 6*SSC, 0.5% SDS, 5*Denhardt solution, 100 μg single stranded herring sperm DNA at 65° C. Filters were washed in 1*SSC, 0.1% SDS at 65° C. Eight plaques, which scored positive for hybridization to the probe on both duplicate sets of filters, were purified according to standard methods and DNA of four positive plaques was isolated using standard procedures.

1.4: Characterization of the *Aspergillus niger* sox gene

1.4.1 Physical mapping of four overlapping λ-clones containing the *Aspergillus niger* sox gene The inserts of the four positive clones were analyzed by Southern hybrization of single and combined digestions with the restriction enzymes EcoRI, SalI, KpnI, HindIII, BglII, NsiI and NcoI, using either oligonucleotide SOX05WM (SEQ ID NO: 11) or the PCR fragment as a probe. Combination of the resulting data with the known locations of SalI and KpnI sites within the part of the gene comprised by the PCR fragment and the length of the sox mRNA as identified under section 1.3.2, led to identification of a 2.5 kb EcoRI fragment and a 6.4 kb NsiI fragment which comprise the entire *Aspergillus niger* sox gene (FIG. 6).

1.4.2 Sequencing the *Aspergillus niger* sox gene

Figure 12:
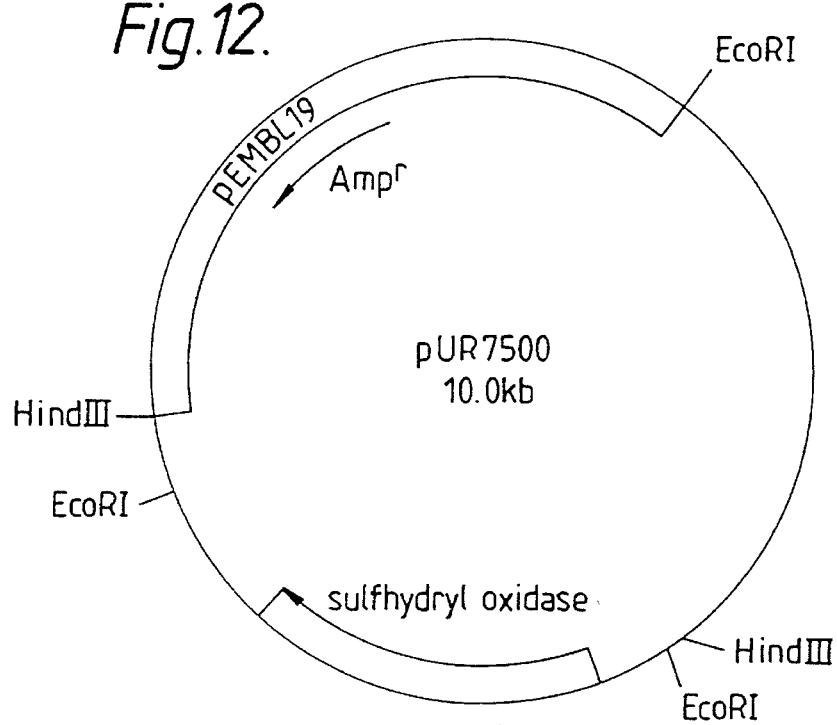
FIG. 12: Map of plasmid pUR7500, comprising the *A. niger* sox gene
Figure 13:
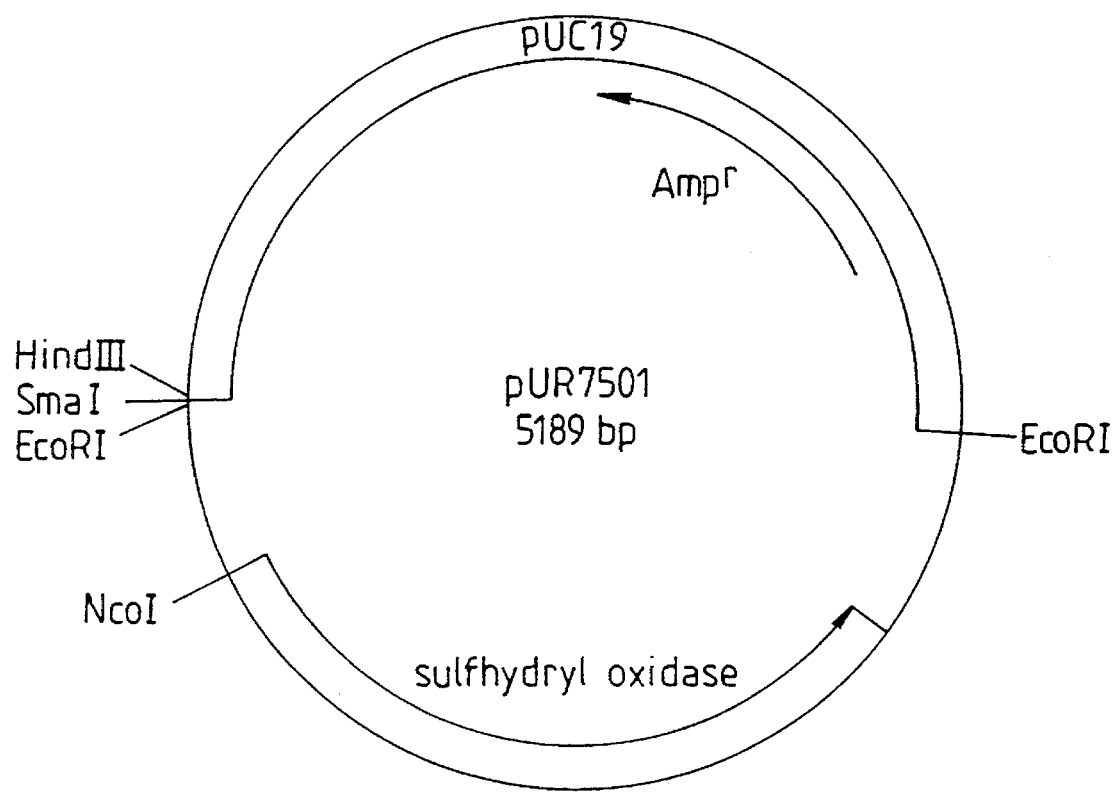
FIG. 13: Map of plasmid pUR7501, comprising the *A. niger* sox gene

The 6.4 kb NsiI fragment from the positive λ-clones, comprising the entire *A. niger* sox gene was subcloned in the PstI site of pEMBL19, yielding pUR7500 (FIG. 12). An *Escherichia coli* JM109 strain containing this plasmid (CBS196.92) was deposited at the Centraal Bureau voor Schimmelcultures (CBS) in Baarn, the Netherlands on Apr. 9th, 1992. The EcoRI 2.5 kb fragment from the positive λ-clones, comprising the entire *A. niger* sox gene was subcloned in the EcoRI site of M13mp19 (Yannish-Perron et al., 1985), and also in the EcoRI site of pUC19 (Yannish-Perron et al., 1985), yielding pUR7501. An *Escherichia coli* JM109 strain containing this plasmid (CBS197.92) was deposited at the Centraal Bureau voor Schimmelcultures (CBS) in Baarn, the Netherlands on Apr. 9th, 1992. The sequence of the EcoRI 2.5 kb fragment was determined by sequencing the entire fragment in both directions according to the method of Sanger using dedicated synthetic primers. Additional sequence information for the region upstream of the structural sox gene was obtained from partial sequencing of the NsiI fragment in pUR7500 (FIG. 7, sequence listing no. 1).

1.4.3 Identification of the open reading frame of the *Aspergillus niger* sox gene In order to identify the exact size and location of introns in the *Aspergillus niger* sox gene, the total RNA isolate of an *Aspergillus niger* NW101 culture after 55 hrs of cultivation (see section 1.3.2) was used for the generation of cDNA, using a ZAP-cDNA synthesis kit (Stratagene, La Jolla) and a dedicated primer (SOXTTT (SEQ ID NO: 7): 5'-GAG-GATCCGTCGACTACTGACTTTTTTTTTTTTTTTTTTTT-3' sequence listing no. 7) for synthesis of single stranded cDNA starting at the poly A-tail of the mRNA. The resulting single strand cDNA preparation was used as a template for the in vitro amplification of specific parts of the sox gene by PCR essentially as described in section 1.3.1. Using a combination of SOX04WM (SEQ ID NO: 10) and SOX06WM (SEQ ID NO: 12) as primers, a fragment of approximately 870 bp was selectively amplified, and using a combination of SOX24WM (SEQ ID NO: 9) (5'-CCAT-TGCATCCATTGAG-3', sequence listing 9) and SOXAAA (SEQ ID NO: 8) (5'-GAGGATCCGTCGACTACTGAC-3', sequence listing no. 8; complementary to part of SOXTTT (SEQ ID NO: 7)) as primers, a fragment of approximately 630 bp was obtained. Taken together, these partially overlapping cDNA fragments cover the entire sequence encoding mature sox. They were purified by gel electrophoresis and completely sequenced using a standard double-strand DNA sequencing protocol. Comparison of these sequences and the genomic DNA sequence of the Aspergillus niger sox gene (section 1.4.2) unambiguously identified the position and size of two introns (FIG. 7) (SEQ ID NO: 1).

Example II

Overproduction of *Aspergillus niger* SOX in *Aspergillus niger* controlled by regulatory elements of the *Aspergillus niger* sox gene

2.1: Construction of an overproducing strain

In order to create an *Aspergillus niger* strain which is capable of overproducing *Aspergillus niger* SOX, multiple copies of the *Aspergillus niger* sox gene were introduced into a suitable acceptor strain by co-transformation with the *Aspergillus niger* pyrA gene.

2.1.1 Construction of a suitable host strain

As an acceptor strain in transformation experiments *Aspergillus niger* NW128 (cspA1, goxC17, pyrA6, nicA1) was used. The cspA1 mutation (short conidiophores) facilitates the handling of the strain on plates, the gox mutation (no production of glucose oxidase) facilitates the evaluation of SOX production during a fermentation experiment and the production of a pure SOX preparation, the pyrA1 mutation (requirement for uridine) is utilized for the introduction of multiple copies of the sox gene, and the nicA1 mutation (requirement for nicotinamide) facilitates the biologically contained handling of the strain. For the construction of *Aspergillus niger* strain NW128, first *Aspergillus niger* strain NW101 (cspA1, goxC17, pabA1, derived from wild type strain *Aspergillus niger* N400 as described in Witteveen et al., 1990) was crossed according to method of Bos et al. (1988) with *Aspergillus niger* strain N613 (fwnA1, hisD4, lysA7, bioA1, leuA1, nicA1, derived from a cross of *Aspergillus niger* N599 and *Aspergillus niger*. N600 as described by Bos et al.,1988) yielding amongst others *Aspergillus niger* strain NW130 (fwnA1, cspA1, goxC17, nicA1). This strain was crossed with *Aspergillus niger* N593 (cspA1, pyrA6, Goosen et al., 1987) using the method described by Bos et al. (1988) except that from the isolated heterozygous diploid colonies a few spores were streaked directly onto CM-benomyl plates supplemented with 200 mg/l histidine. Among the resulting strains was *Aspergillus niger* strain NW128 (cspA1, goxC17, pyrA6, nicA1).

2.1.2 Co-transformation

*Aspergillus niger* strain NW128 was co-transformed with mixtures of two different DNA fragments in various ratios using standard techniques (e.g Goosen et al., 1987). The two fragments used are the 3.8 kb XbaI fragment of *Aspergillus niger* N400, comprising the entire *Aspergillus niger* pyrA gene and functional promoter (Goosen et al., 1987), and the 2.5 kb EcoRI fragment of *Aspergillus niger* N400, comprising the entire sox gene and flanking sequences (see example I, section 1.4, FIG. 7). The molar ratio of the two fragments was varied so as to obtain pyrA transformed strains containing as many copies of the sox gene as possible (ratios varied from 1:1 to 1:20 for pyrA:sox)

2.1.3 Identification of multicopy transformants

Figure 8:
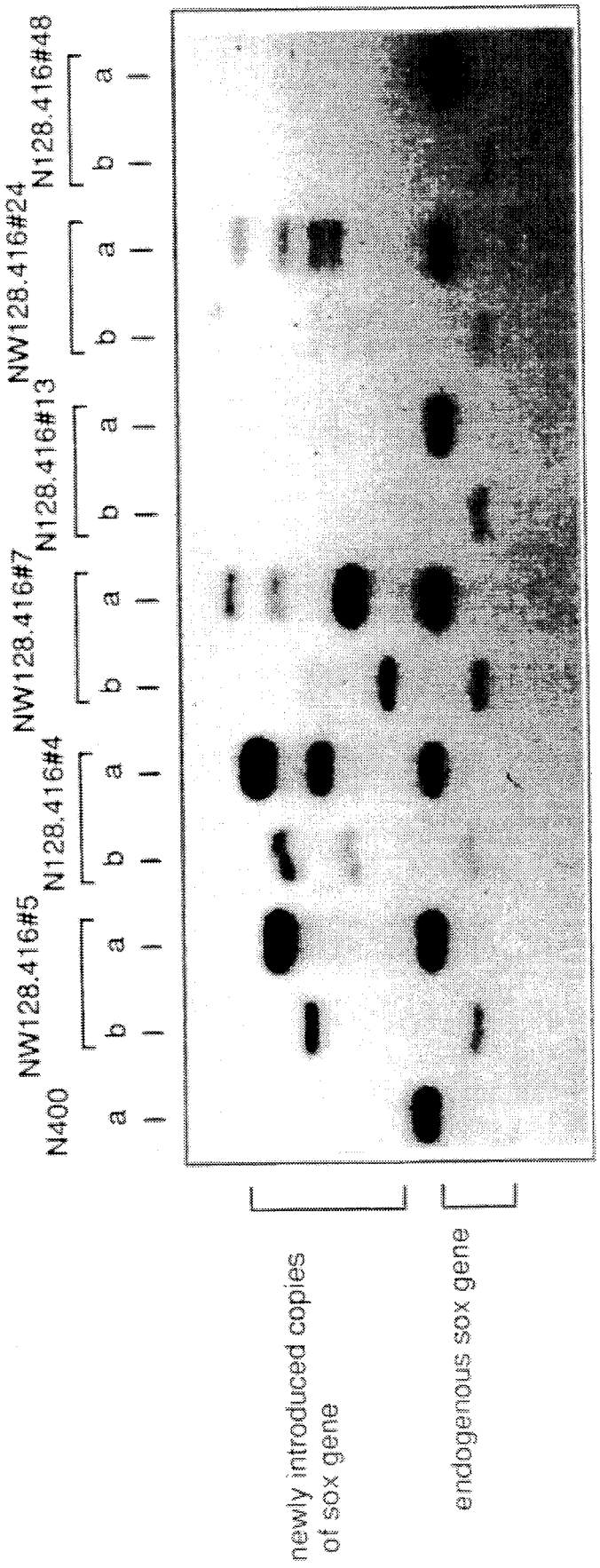
FIG. 8: Southern analysis of *A. niger* transformants with the *A. niger* sox gene.
Figure 9:
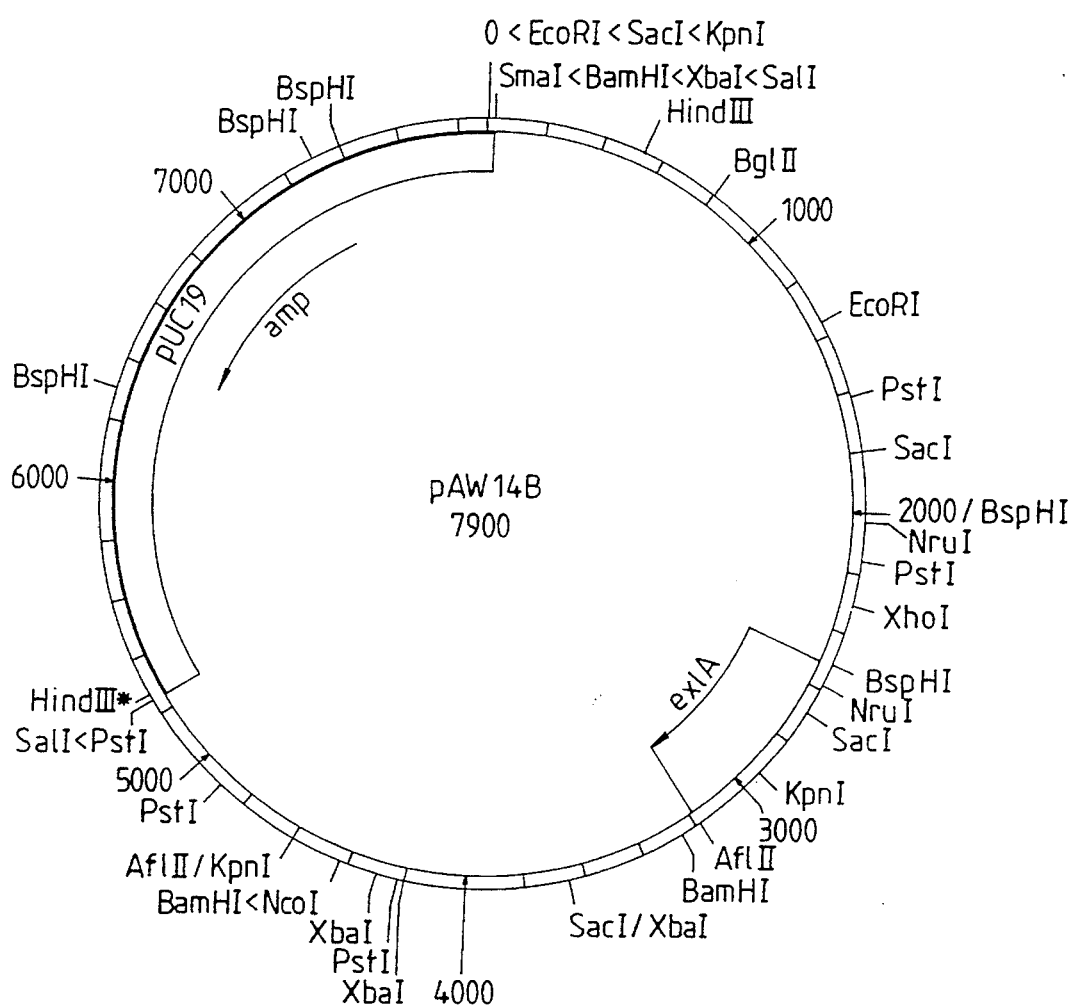
FIG. 9: Map of plasmid pAW14B, comprising the *A. niger* var. awamori exlA gene

Transformed strains, as judged by their ability to grow in the absence of uridine, were grown in rich medium in 100 ml cultures in baffled shakeflasks, and DNA was isolated according to standard methods. HindIII restriction enzyme digests were analyzed by Southern hybrization using the 2.5 kb EcoRI fragment comprising the *Aspergillus niger* sox gene (example I, section 1.4, FIG7) as a probe, and a DNA isolate of *Aspergillus niger* strain N400 as a control (FIG8). From the 6 pyrA positive transformants analyzed in detail, 4 appeared to have incorporated one or more additional copies of the *Aspergillus niger* sox gene, as indicated by the hybridization of the probe to additional bands as compared to the *Aspergillus niger* N400 control. Comparison of the intensity of the hybridization signal corresponding to the endogenous sox gene in lane a (NW128.416 #4) with the intensity of the hybridization signals corresponding to the additionally introduced copies of the sox gene in lane b (NW128.416 #4) reveals that between 5 and 10 additional copies have been introduced in transformant *Aspergillus niger* NW128.416 #4.

2.2: Fermentative overproduction of SOX

Spores were isolated from the multicopy transformant A. niger NW128.416 #4 according to standard methods (e.g. Pontecorvo et al., 1953). A fermentation was performed with these spores parallel to a fermentation of Aspergillus niger NW1O1. Fermentations were performed in standard type 2 liter fermentors containing 1.5 l of a fermentation medium with the following composition (per liter): 40 g fructose, 0.6 g $NaNO_3$, 0.25 g $KH_2PO_4$, 0.1 g $MgSO_4 \cdot 7H_2O$, 0.5 g yeast extract and 20 ml of a trace elements solution (Visniac, 1957). For Aspergillus niger NW128-derived transformants 1 mg per liter nicotinamide was added per liter, whereas 1.4 mg paraaminobenzoic acid per liter was added for Aspergillus niger NW101. During the fermentation the pH was kept at 5.5 by the addition of 5M NaOH, the temperature was kept at 30° C. The $pO_2$ was kept above 30% by switching the gass inlet from air to oxygen when neccesary. Fermentors were inoculated with precultures (20%) of fungal spores. Precultures (two 300 ml conical, baffled shakeflasks containing 150 ml fermentation medium each) were inoculated with fungal spores (3.105 spores/ml) and incubated for 6 hours at 30° C. and 250 rpm in a shaking incubator. The fermentation process was carried out for 50 hr or longer. Production of SOX was measured after 50 hours of fermentation. For the strain containing a single, native copy of the Aspergillus niger sox gene, NW101, the amount of SOX produced was 34 U/l, whereas in case of the strain comprising additional copies of the Aspergillus niger sox gene, NW128.416 #4, 150 U/l had been produced. Thus, overproduction of Aspergillus niger SOX can be achieved by the introduction of additional copies of the Aspergillus niger sox gene in the Aspergillus niger genome.

Example III

Overproduction of Aspergillus niger SOX in Aspergilli controlled by other regulatory elements than those derived from the Aspergillus niger sox gene The regulation of the production of SOX in Aspergillus niger is such that appreciable levels of SOX activity can only be detected at relatively late stages of growth. To further increase the production level of SOX alternative regulation signals can be used. As an example the coding region of the sox gene was detached from the upstream control regions (comprising a.o. the promoter), and placed under the control of the promoter derived from the endoxylanase II gene (exlA) of A. niger var. awamori CBS 115.52 (exlA promoter) by fusion at the ATG-translational start signal. Other promoters derived from Aspergillus strains can also be used, and the constructions for using the promoters derived from the glucoamylase (glaA) gene from A. niger CBS 120.49 (glaA promoter) and the glyceraldehyde-3-phosphate-dehydrogenase (gpdA) gene from A. nidulans (gpdA promoter) will be outlined.

3.1: exlA promoter

Figure 10:
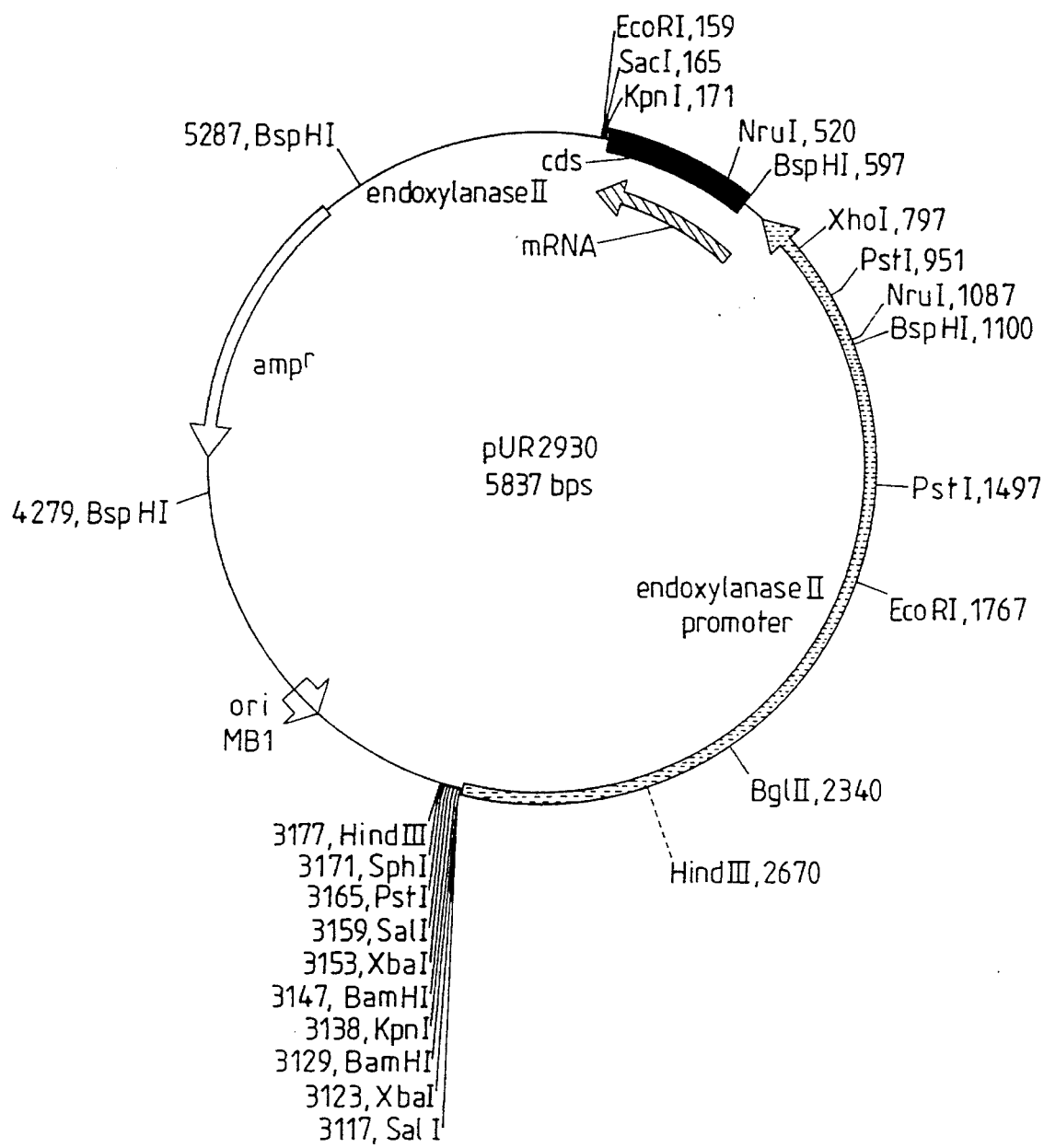
FIG. 10: Map of plasmid pUR2930, comprising the promoter region of the *A. niger* var. *awamori* exlA gene
Figure 11:
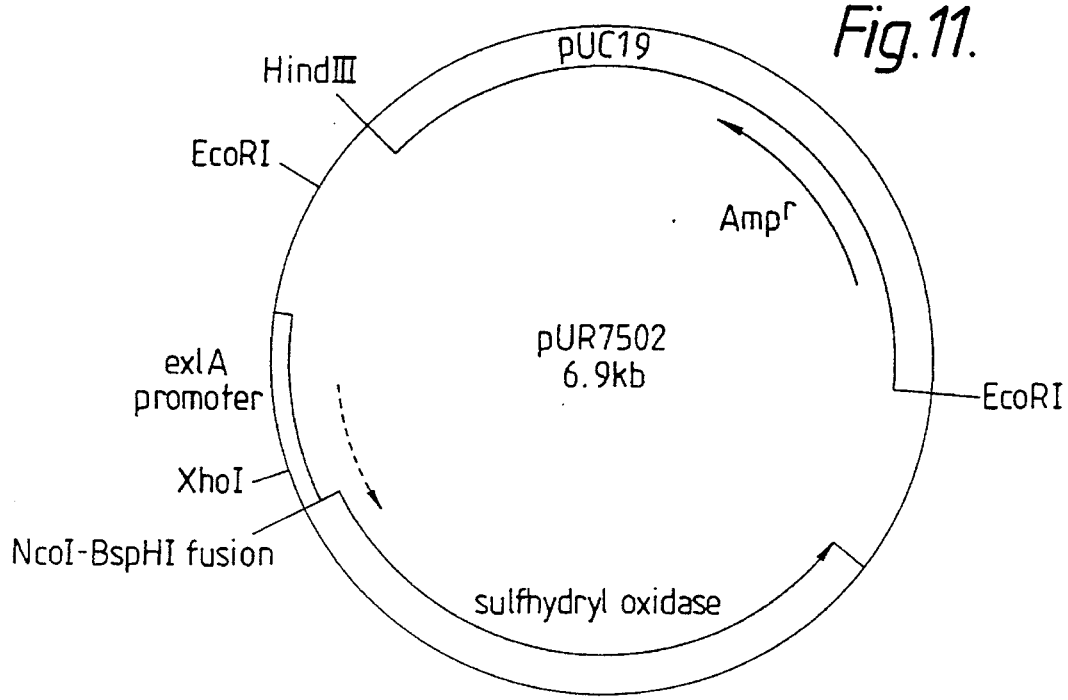
FIG. 11: Map of plasmid pUR7502, comprising the *A. niger* sox gene under the regulation of the exlA promoter

The 3.0 kb KpnI fragment of pAW14B (described in van Gorcom et al., 1991) was inserted in the KpnI site of pTZ19R, yielding pUR2930 (FIG10). The 1.9 kb HindIII-XhoI fragment and the 200 bp XhoI-BspHI fragment of pUR2930 were combined with the 4.8 kb NcoI-HindIII fragment of pUR7501, yielding pUR7502 (FIG. 11). This plasmid comprises the A. niger sox gene fused to the A. niger var. awamori exlA promoter at the ATG-translational start signal at the fusion of the BspHI and NcoI sites (FIG11).

This plasmid and suitable fragments thereof can be used together with the 3.8 kb XbaI-fragment of the A. niger pyrA gene in co-transformations of A. niger NW128, essentially as described in example II, section 2.1.2. Transformants with a $PYR^+$ phenotype can be screened for the presence of multiple copies of the sox gene, essentially as described in example II, section 2.1.3, which is facilitated by the differences in the length of fragments generated by suitable restriction enzyme digestions between the endogenous copy of the sox gene and the copies behind the exlA promoter that are newly introduced. Alternatively, the amdS gene of A. nidulans can be inserted in pUR7502, and used in transformation experiments for selection of transformants containing multiple copies of the sox gene.

Transformants containing multiple copies of the newly introduced A. niger sox gene behind the A. niger var. awamori promoter can be grown in media that induce increased transcription levels from the exlA promoter, for example media containing wheat bran or xylan as described in patent application WO 91/19782 (Van Gorcom et al., 1991), provided that, when using A. niger NW128 as a host strain, these media are supplemented with 1 mg/l nicotinamide.

As a further example, plasmid pUR7502 and suitable fragments thereof were introduced in A. niger var. awamori CBS 115.52. To this end a $pyrA^-$ variant of A. niger var. awamori CBS 115.52 was constructed using UV-mutagenesis and screening on fluoroorotic acid plates (3,106 spores were irradiated for 90 seconds at 20 erg/mm2/sec with UV-radiation, yielding 44% survival). Within the obtained group of $pyr^-$ variants two complementation groups could be identified by transformation with the 3.8 kb XbaI fragment of Aspergillus niger N400, comprising the entire Aspergillus niger pyrA gene and functional promoter (Goosen et al., 1987). A $pyrA^-$ variant of A. niger var. awamori CBS 115.52 that could be complemented by the Aspergillus niger pyrA gene was identified and named strain NW208. Multiple copies of the fusionconstruct comprising the A. niger sox gene under the control of the exlA promoter were introduced in this strain by co-transformation of the 3.3 kb EcoRI fragment of pUR7502 comprising the sox gene and the 3.8 kb XbaI-fragment of the A. niger pyrA gene, essentially as described in example II, section 2.1.2. Transformants with a $PYR^+$ phenotype were screened for the presence of multiple copies of the sox gene, essentially as described in example II, section 2.1.3. By this procedure transformant AW498-9 was identified, which comprises multiple copies of the A. niger sox gene under the control of the exlA promoter.

Aspergillus niger var. awamori CBS 115.52 (AW) and transformant AW498-9 were grown under the following conditions: baffled shake flasks (500 ml) with 200 ml synthetic media (pH 6.5 with KOH) were inoculated with spores (final concentration: $10^6$/ml). The medium had the following composition (AW Medium):

| | | | |
|---|---|---|---|
| sucrose | 10 g/l | $NaNO_3$ | 6.0 g/l |
| KCl | 0.52 g/l | $KH_2PO_4$ | 1.52 g/l |
| $MgSO_4.7H_2O$ | 0.49 g/l | Yeast extract | 1.0 g/l |
| $ZnSO_4.7H_2O$ | 22 mg/l | $H_3BO_3$ | 11 mg/l |
| $MnCl_2.4H_2O$ | 5 mg/l | $FeSO_4.7H_2O$ | 5 mg/l |
| $CaCl_2.6H_2O$ | 1.7 mg/l | $CuSO_4.5H_2O$ | 1.6 mg/l |
| $NaH_2MoO_4.2H_2O$ | 1.5 mg/l | $Na_2EDTA$ | 50 mg/l |

Incubation took place at 30° C., 125 rpm for 24 hours in a Mk X incubator shaker. After growth cells were collected by filtration (0.45 μm filter), washed twice with AW Medium without sucrose and yeast extract (salt solution), transferred to 500 ml shake flasks and resuspended in 100 ml salt solution to which xylose has been added to a final concentration of 10 g/l (induction medium). The moment of resuspension is referred to as "t=0" (start of induction) and the cultures were incubated at 30° C., 150 rpm in a Mk X incubator shaker. Samples were taken 15, 23 and 46 hours after induction. Biomass was removed by filtration over miracloth and SOX activity in the supernatants was determined as outlined in example I (see table A).

TABLE A

SOX production under the control of the exlA promoter.

| Strain | exp. | t = 0 | t = 15 | t = 23 | t = 46 |
|--------|------|-------|--------|--------|--------|
| AW | A | 28 | 27 | 52 | 203 |
| AW | B | 38 | 31 | 48 | 187 |
| AW498-8 | A | 34 | 3240 | 3210 | 3720 |
| AW498-9 | B | 28 | 2980 | 3100 | 3430 |

Transformants were grown on synthetic medium as indicated in the text for 24 hours and at t=0 were transferred to induction medium as indicated in the text. SOX activity in the medium was determined as described in the text and is expressed in units per liter. A and B represent independent duplo experiments.

From Table A it is evident that that SOX can be efficiently produced in A. niger var. awamori using the exlA promoter, which is specifically induced by the presence of xylose. Under these conditions the production of glucose oxidase activity by this strain is low and the production of SOX in the transformed strain is very high and commences very soon after induction.

Moreover, following the approach outlined above, plasmid pUR7502 and suitable fragments or plasmids derived therefrom, can be used for the introduction of multiple copies of the A. niger sox gene under the control of the exlA promoter into strains of other species of the genus Aspergillus, for example A. oryzae, A. sojae, A. tubigensis, A. japonicus, A. aculeatis, A. awamori, A. nidulans, etc.

3.2: glaA promoter

An approach similar to that outlined in section 3.1 can also be followed for the construction of plasmids in which the A. niger sox gene has been fused to the promoter of the A. niger glaA gene at the ATG-translational start signal. In this case the 7.35 kb BssHII-XmnI fragment of pAN52-6 (Van den Hondel et al., 1990) or other fragments comprising the functional glaA promoter can be combined with the 4.8 kb HindIII-NcoI fragment of pUR7501 in the proper orientation, together with synthetic oligonucleotides to restore the glaA promoter sequence just upstream of the ATG-translational start signal, essentially as described in patent application WO 91/19782 (Van Gorcom et al., 1991). The resulting plasmids or suitable fragments thereof can be used to generate transformants containing multiple copies of the A. niger sox gene under the control of the A. niger glaA promoter in strains of species of the genus Aspergillus carrying genetic markers, essentially as outlined in section 3.1 of this example.

3.3: gpdA promoter

An approach similar to that outlined in section 3.1 can also be followed for the construction of plasmids in which the A. niger sox gene is fused to the promoter of the A. nidulans gpdA gene at the ATG-translational start signal, essentially as outlined in patent application WO 91/19782 (Van Gorcom et al., 1991). For this purpose the 1.8 kb StuI-NcoI fragment of pAN52-1 (Punt et al., 1987), comprising the gpdA promoter sequences up to the ATG-translational start signal, can be ligated with the 4.8 kb SmaI-NcoI fragment of pUR7501. The resulting plasmids or suitable fragments thereof can be used to generate transformants containing multiple copies of the A. niger sox gene under the control of the A. nidulans gpdA promoter in strains of species of the genus Aspergillus carrying genetic markers, essentially as outlined in section 3.1 of this example.

Example IV

Production of Aspergillus niger SOX in yeast

For the production of Aspergillus niger SOX in yeasts, vectors can be constructed in which the sequences encoding the mature A. niger SOX protein are placed under the control of known yeast promoters. Since yeasts may not be capable to correctly remove the introns from the primary RNA transcript of the A. niger sox gene, the introns should be removed in these constructions. This can be accomplished by making use of the overlapping cDNA fragment of the A. niger sox gene which were described in example I, section 1.4.3. A cDNA fragment covering the entire A. niger sox mRNA from the part encoding the N-terminus of the mature protein to the poly A tail can be synthetized from these two fragments by a PCR reaction. The resulting fragment can be used, by using PCR or synthetic oligonucleotides, to make functional fusions of the A. niger cDNA copy of the sox mRNA to yeast promoters and functional sequences, such as translational start signals and, if secretion of the A. niger SOX protein is desired, functional yeast signal sequences derived from yeast genes encoding proteins that are efficiently secreted. Such constructions can be incorporated in either autonomously replicating yeast vectors, or alternatively, in yeast vectors that are capable of integration in the yeast genome in single or multiple copies. The levels of expression of the A. niger sox gene directed by such constructions can be further improved by adjustment of the codon usage of the A. niger sox gene according to the codon preferences known for yeasts.

Example V

Use of sulfhydryl oxidase to prevent overmixing during wheat dough preparation

Figure 14C:
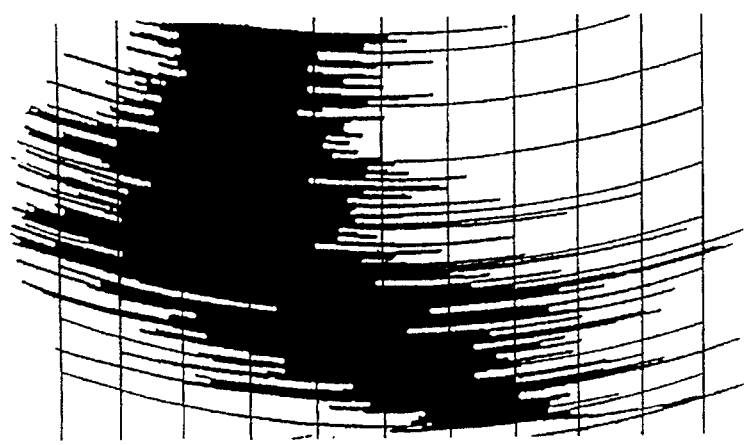
FIG. 14: Mixograph experiments in the absence and presence of SOX
Figure 14B:
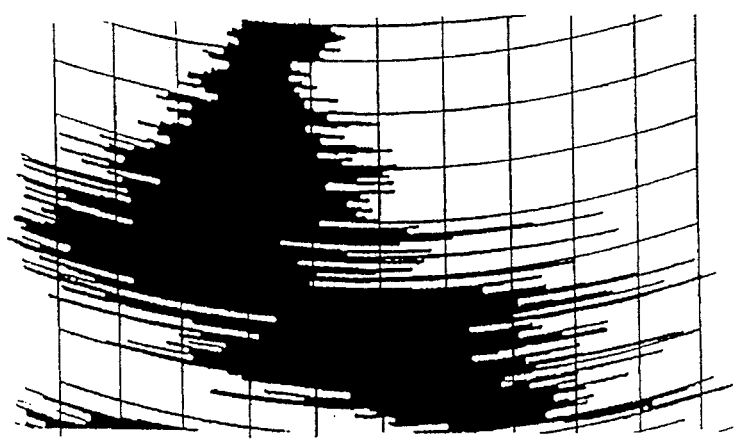
Figure 14A:
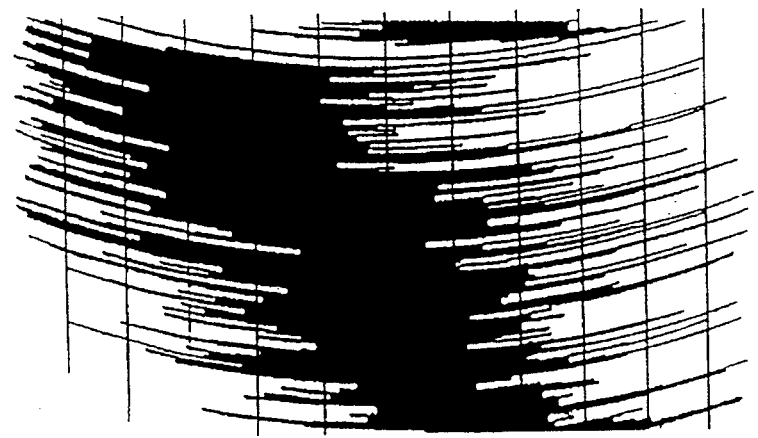

In order to obtain a dough with good handling properties and a good baked product it is essential to "fully develop" the dough by kneading. In this dough the flour particles are fully hydrated, the free water is at a minimum, and the dough is at its point of minimum mobility and maximum resistance to extension. Mixing past this point is certainly not beneficial and if continued causes negative changes in the physical properties of the dough and the quality of the final baked product. During the kneading process the gluten proteins (glutenins and gliadins) are dis-aggregated or de-polymerized, and again aggregated or polymerized. Breaking of disulfide cross links between especially the high molecular weight glutenin subunits through reduction or formation of thiyl radicals, followed by the reformation of disulfide cross links through annihilation or oxidation is presumed to play an important role in the formation of a continuous gluten matrix. Low molecular weight thiol-containing compounds such as cysteine or glutathione (also naturally present in flour) are known to affect the gluten matrix formation, and they are widely used to reduce the mixing time. A disadvantage of the addition of these type of compounds is that they make the dough more critical to overmixing, or overdevelopment. Addition of sulfhydryl oxidase to dough in conjunction to these type of thiol-containing compounds can prevent the overmixing, while retaining the full reduction in mixing time. The effect is demonstrated in the following experiment. 10 gram Columbus flour (Meneba Mills, Rotterdam, the Netherlands) is mixed with 6 ml water, 0.2 gram bakers yeast (koningsgist ex Gist-Brocades, the Netherlands) and 0.2 gram sodium chloride in a Mixograph (National Manufacturing, Nebr., U.S.A.) and dough development was followed by measuring the increase in resistance. Panel A of FIG. 14 shows the resistance chart for a dough without any additions; full development takes circa 4 minutes. 50 mg/kg 2-mercaptoethanol have been added to the dough in panel B of FIG. 14, which reduces the dough development to circa 2 minutes. Further mixing however gives an overmixed dough with a typical resistance trace as shown. In panel C of FIG. 14 the dough contains 50 mg/kg 2-mercaptoethanol and 0.1 mg purified sulfhydryl oxidase (200 U/mg). Clearly overmixing is severely reduced. The same effects could be shown for the addition of glutathione, cysteine, thio-glucose and other low molecular weight thiol-containing compounds. The end result is a dough that has obtained tolerance to (over)mixing.

Example VI

Use of sulfhydryl oxidase for strengthening wheat dough

The gluten matrix formed after kneading a wheat dough is responsible for the visco-elastic behaviour of that dough. Carbondioxide formed by the bakers yeast added will be retained by such a dough and a leavening effect occurs. Gas retention is considerably influenced by the strength of the gluten matrix, which is partly related to the gluten content, but is also partly related to the disulfide cross-linking between the glutenin molecules. Glutathione or other low molecular weight thiol-containing compounds can have a deteriorating effect on the cross-linking as described in the example above. To illustrate the beneficial effect of sulfhydryl oxidase according to this invention the following example is given. Microloaves were prepared using 10 gram Columbus flour (Meneba Mills, Rotterdam, the Netherlands), 6 ml water, 0.2 g sodium chloride and 0.2 gram bakers yeast (koningsgist ex Gist Brocades, the Netherlands). Doughs were mixed in a Mixograph (National Manufacturing, Nebr., U.S.A.) for 4 minutes at 25° C., proofed for a total of 155 minutes at 30° C., with gas redistribution after, 40 and 80 minutes. The loaves were baked for 10 minutes at 240° C. Volumes of the loaves were measured by the seed displacement technique. The following specific volumes were obtained (ml/g) as a function of variation in the amount of glutathione added with or without supplementation with sulfhydryl oxidase at 5 mg/kg (200 U/mg).

| GSH mg/kg | SV no SOX | SV with SOX |
|---|---|---|
| 0 | 3.8 | 3.8 |
| 50 | 3.2 | 4.2 |
| 100 | 2.8 | 3.9 |
| 150 | 2.5 | 3.9 |
| 200 | ND | 3.5 |
| 300 | ND | 3.5 |

ND is not determined as these doughs could no longer be handled. Clearly the sulfhydryl oxidase added to the doughs is capable of retaining the gas holding capacity of the dough.

References cited in the Examples

1 Maniatis, T., E. F. Frisch and J. Sambrook (1982). Molecular cloning: a laboratory manual. Cold Spring Harbor Laboratory, Cold Spring Harbor, N.Y.

2 De Graaff, L. H., H. W. J. van den Broek and J. Visser (1988). Isolation and expression of the *Aspergillus nidulans* pyruvate kinase gene. Curr. Genet. 13:315–321.

3 De la Motte, R. S. and F. W. Wagner (1987). *Aspergillus niger* Sulphydryl Oxidase. Biochemistry 26:7363–7371.

4 Witteveen, C. F. B., P. van de Vondervoort, K. Swart and J. Visser (1990). Glucose oxidase overproducing and negative mutants of *Aspergillus niger*. Appl. Microbiol. Biotechnol. 33:683–686.

5 Visniac, W. and M. Santer. (1957). Bacteriol. Rev. 21: pp 195–237.

6 Pontecorvo, G., J. A. Roper, L. J. Hemmons, K. D. MacDonald and A. W. J. Bufton (1953). The genetics of *Aspergillus nidulans*. Adv. Genet. 5:141–239.

7 Barratt, R. W., G. B. Johnson and W. N. Ogata (1965). Wild-type and mutant stocks of *Aspergillus nidulans*. Genetics 52:233–246.

8 Harmsen, J. A. M., M. A. Kusters-van Someren and J. Visser (1990). Cloning and expression of a second *Aspergillus niger* pectin lyase gene (pelA): Indications of a pectin lyase gene family in *A. niger*. Curr. Genet. 18:161–166.

9 Yannish-Perron, C., J. Vieira and J. Messing (1985). Improved M13 phage cloning vectors and host strains: nucleotide sequences of the M13mp18 and pUC19 vectors. Gene 33: 17-12.

10 Bos, C, J., A. J. M. Debets, K. Swart, A. Huybers, G. Kobus and S. M. Slakhorst (1988). Genetic analysis and the construction of master strains for assignment of genes to six linkage groups in *Aspergillus niger*. Curr. Gene. 14:437–443.

11 Goosen, T., G. Bloemheuvel, C. Gysler, D. A. de Bie, H. W. J. van den Broek and K. Swart (1987). Transformation of *Aspergillus niger* using the homologous orotidine-5'-phosphate-decarboxylase gene. Curr. Genet. 11:499–503.

12 Van Gorcom, R. F. M., J. G. M. Hessing, J. Maat, M. Roza and J. Verbakel (1991). Endoxylanase II production. Patent application WO 91/19782

13 Van den Hondel, C. A. M. J. J., P. J. Punt and R. F. M. van Gorcom (1991). Heterologous gene expression in filamentous fungi. In: More Gene Manipulations, J. W. Bennett and L. L. Lasure (Ed), Academic Press, Inc., San Diego.

14 Punt, P. J., R. P. Oliver, M. A. Dingemanse, P. H. Pouwels and C. A. M. J. J. van den Hondel (1987). Transformation of Aspergillus based on the hygromycin B resistance marker from *Escherichia coli*. Gene 56:117–124.

We claim:

1. A recombinant DNA material comprising a nucleotide sequence encoding a ripening form of a polypeptide having sulfhydryl oxidase activity wherein the nucleotide sequence is SEQ ID NO:1 or agenetic variant thereof encoding the same polypeptide.

2. A host cell comprising the recombinant DNA material as claimed in claim 1, such that said cell expresses a nucleotide sequence encoding a ripening form of a polypeptide having sulfhydryl oxidase activity as encoded by said recombinant DNA material under suitable conditions.

3. A process for producing a ripening form of a polypeptide with sulfhydryl oxidase activity comprising culturing a cell as claimed in claim 2 and optionally isolating the resulting ripening form of a polypeptide having sulfhydryl oxidase activity.

4. A nucleotide sequence which hybridizes to SEQ ID NO:1 or a genetic variant thereof encoding the same polypeptide, said hybridization being performed in 6 X SSC, 0.5% SDS, 5 X Denhardt solution, 100 microgram single strand herring sperm DNA at 65° C., followed by a wash step in 1 X SCC, 0.1% SDS at 65° C., said nucleotide sequence encoding a ripening form of a polypeptide having sulfhydryl oxidase activity.

5. A recombinant DNA material according to claim 1, wherein the nucleotide sequence encoding the ripening form of polypeptide is derived from human milk, bovine milk, kidney homogenate, mammalian pancreas, rat skin, fungus *Mirithecium varrucaria, Dactylium dendroides, Aspergillus sojae, Aspergillus niger, Aspergillus oryzae, Bacillus subtilis, Penicillium lilacinum, Bacillus licheniformis, Bacillus coagulans, Bacillus stearothermophilis, Mucor miehei*, or *Trichoderma reesei*.

6. A recombinant DNA material according to claim 1, wherein the nucleotide sequence encoding the ripening form of polypeptide is derived from the group of microbial organisms consisting of *Mirithecium varrucaria, Dactylium dendroides, Aspergillus, Bacillus subtilis, Penicillium lilacinum, Bacillus licheniformis, Bacillus coagulans, Bacillus stearothermophilis, Mucor miehei*, or *Trichoderma reesei*.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
( A ) LENGTH: 2563 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Aspergillus niger
( B ) STRAIN: CBS 120.49

( v i i ) IMMEDIATE SOURCE:
( B ) CLONE: pUR7500, pUR7501

( i x ) FEATURE:
( A ) NAME/KEY: exon
( B ) LOCATION: 477..702

( i x ) FEATURE:
( A ) NAME/KEY: intron
( B ) LOCATION: 703..769

( i x ) FEATURE:
( A ) NAME/KEY: exon
( B ) LOCATION: 770..1573

( i x ) FEATURE:
( A ) NAME/KEY: intron
( B ) LOCATION: 1574..1681

( i x ) FEATURE:
( A ) NAME/KEY: exon
( B ) LOCATION: 1682..1830

( i x ) FEATURE:
( A ) NAME/KEY: CDS
( B ) LOCATION: join(477..702, 770..1573, 1682..1830)

( i x ) FEATURE:
( A ) NAME/KEY: sig_peptide
( B ) LOCATION: 477..533

( i x ) FEATURE:
( A ) NAME/KEY: promoter
( B ) LOCATION: 1..476

( i x ) FEATURE:
( A ) NAME/KEY: terminator
( B ) LOCATION: 1831..2563

( i x ) FEATURE:
( A ) NAME/KEY: mat_peptide
( B ) LOCATION: join(534..702, 770..15731682..1827)
( D ) OTHER INFORMATION: /product="Sulfhydryl oxidase"
/ gene="SOX"

( x i ) SEQUENCE DESCRIPTION: SEQ ID NO: 1:

```
GCATCTGGGC  CCTCTTCCAC  TTGCATGCAC  TATTGAAATC  CCAGCCCTGC  CGATCGAATT    60
CCGCCGATCT  TGGCAGCATC  CAACCGGGAT  TTGAAGCCAC  TGCAGTCATC  GACTCTCATT   120
CGGCAGGTCG  ACTCTAGTCT  CCCCAACCAT  ATTCTCAATA  ATCTTCTCTT  TACCTTGGCA   180
CGGCGGACCC  CGAACTGGAC  TGGCACGGAA  TCGATCGTGT  CGATCCCCTT  CAGCTGCTCC   240
```

| | | | | | | | | | | |
|---|---|---|---|---|---|---|---|---|---|---|
| ACCAGCTCGA | GTCTTGGCTG | CATCCCAGCT | GAATCACCAA | ATCCTGCTCC | TCGGCCTCGG | | | | | 300 |
| ACAACTTGGG | ACGATGTGCG | TGCTGCACTG | TCCCTTGAGG | AACATGCTGT | TGTGGAGGTA | | | | | 360 |
| TAAAGACAGC | TTGAAAGCTG | CTGCTGCTGC | TGCATCTTCT | TCTCGGCAGA | CTGCAGCAGG | | | | | 420 |
| CCTTCTCTCT | TCTTCAGTGC | GTGGGGAACG | ATCCGATCCG | TAACCTAGTC | CACACC | | | | | 476 |

```
ATG  GCT  CCC  AAG  TCC  CTC  TTT  TAT  TCC  CTC  TTC  TCC  ACC  ATC  AGC  GTC        524
Met  Ala  Pro  Lys  Ser  Leu  Phe  Tyr  Ser  Leu  Phe  Ser  Thr  Ile  Ser  Val
-19            -15                 -10                           -5

GCT  CTG  GCG  TCG  TCC  ATC  CCC  CAG  ACC  GAT  TAC  GAT  GTG  ATT  GTC  GTG        572
Ala  Leu  Ala  Ser  Ser  Ile  Pro  Gln  Thr  Asp  Tyr  Asp  Val  Ile  Val  Val
               1                   5                             10

GGA  GGA  GGT  CCC  GCG  GGC  CTC  AGT  GTC  TTG  AGC  AGT  CTC  GGG  CGC  ATG        620
Gly  Gly  Gly  Pro  Ala  Gly  Leu  Ser  Val  Leu  Ser  Ser  Leu  Gly  Arg  Met
     15                      20                       25

AGA  CGG  AAG  ACC  GTG  ATG  TTC  GAC  TCG  GGA  GAA  TAC  CGT  AAT  GGT  GTT        668
Arg  Arg  Lys  Thr  Val  Met  Phe  Asp  Ser  Gly  Glu  Tyr  Arg  Asn  Gly  Val
30                      35                       40                           45

ACG  CGC  GAG  ATG  CAC  GAT  GTC  CTT  GGC  TTT  GAT       G GTAATTTCTG             712
Thr  Arg  Glu  Met  His  Asp  Val  Leu  Gly  Phe  Asp
                    50                            55
```

| | | |
|---|---|---|
| CCTCATTTAC CCCAGGATCT CCCATTTCAT GTCAATTTAT ACCTAACATC CACAAAG | GC<br>Gly | 771 |

```
ACT  CCA  CCT  GCC  CAA  TTC  CGT  GGC  CTC  GCC  CGC  CAG  CAG  ATC  TCT  AAA       819
Thr  Pro  Pro  Ala  Gln  Phe  Arg  Gly  Leu  Ala  Arg  Gln  Gln  Ile  Ser  Lys
                60                       65                       70

TAC  AAC  TCG  ACC  AGC  GTC  ATC  GAC  ATC  AAG  ATC  GAC  TCC  ATC  ACC  CCG       867
Tyr  Asn  Ser  Thr  Ser  Val  Ile  Asp  Ile  Lys  Ile  Asp  Ser  Ile  Thr  Pro
     75                       80                       85

GTC  GAG  GAT  GCC  GCA  GCC  AAC  AGC  TCA  TAC  TTC  CGT  GCC  GTC  GAC  GCC       915
Val  Glu  Asp  Ala  Ala  Ala  Asn  Ser  Ser  Tyr  Phe  Arg  Ala  Val  Asp  Ala
90                       95                      100                           105

AAC  GGC  ACA  CAA  TAC  ACC  TCC  CGC  AAG  GTA  GTC  CTG  GGT  ACC  GGG  CTG       963
Asn  Gly  Thr  Gln  Tyr  Thr  Ser  Arg  Lys  Val  Val  Leu  Gly  Thr  Gly  Leu
               110                      115                           120

GTC  GAC  GTG  ATC  CCT  GAT  GTG  CCC  GGT  CTC  CGC  GAA  GCC  TGG  GGC  AAG      1011
Val  Asp  Val  Ile  Pro  Asp  Val  Pro  Gly  Leu  Arg  Glu  Ala  Trp  Gly  Lys
               125                      130                           135

GGC  ATC  TGG  TGG  TGT  CCC  TGG  TGT  GAC  GGC  TAC  GAG  CAC  CGC  GAC  GAG      1059
Gly  Ile  Trp  Trp  Cys  Pro  Trp  Cys  Asp  Gly  Tyr  Glu  His  Arg  Asp  Glu
               140                      145                           150

CCC  CTC  GGT  ATC  CTA  GGT  GGG  TTG  CCG  GAC  GTG  GTC  GGC  AGC  GTC  ATG      1107
Pro  Leu  Gly  Ile  Leu  Gly  Gly  Leu  Pro  Asp  Val  Val  Gly  Ser  Val  Met
     155                      160                           165

GAA  ACC  CAC  ACC  CTG  TAC  TCG  GAC  ATC  ATC  GCT  TTC  ACT  AAC  GGC  ACC      1155
Glu  Thr  His  Thr  Leu  Tyr  Ser  Asp  Ile  Ile  Ala  Phe  Thr  Asn  Gly  Thr
170                      175                      180                           185

TAC  ACG  CCC  GCC  AAC  GAA  GTC  GCC  CTG  GCA  GCC  AAG  TAC  CCG  AAC  TGG      1203
Tyr  Thr  Pro  Ala  Asn  Glu  Val  Ala  Leu  Ala  Ala  Lys  Tyr  Pro  Asn  Trp
                    190                      195                           200

AAG  CAG  CAG  CTC  GAA  GCG  TGG  AAT  GTC  GGT  ATT  GAC  AAC  CGC  TCC  ATT      1251
Lys  Gln  Gln  Leu  Glu  Ala  Trp  Asn  Val  Gly  Ile  Asp  Asn  Arg  Ser  Ile
               205                      210                           215

GCA  TCC  ATT  GAG  CGT  CTC  CAA  GAT  GGA  GAT  GAC  CAC  CGC  GAC  GAC  ACG      1299
Ala  Ser  Ile  Glu  Arg  Leu  Gln  Asp  Gly  Asp  Asp  His  Arg  Asp  Asp  Thr
               220                      225                           230

GGT  AGA  CAG  TAC  GAC  ATC  TTC  CGG  GTC  CAT  TTC  ACC  GAT  GGC  TCC  AGC      1347
Gly  Arg  Gln  Tyr  Asp  Ile  Phe  Arg  Val  His  Phe  Thr  Asp  Gly  Ser  Ser
     235                      240                           245

GTT  GTA  CCG  AAC  ACC  TTC  ATC  ACA  AAC  TAC  CCG  ACC  GCC  CAG  CGT  TCC      1395
```

| | | | | | | | | | | | | | | | | |
|---|---|---|---|---|---|---|---|---|---|---|---|---|---|---|---|---|
| Val | Val | Pro | Asn | Thr | Phe | Ile | Thr | Asn | Tyr | Pro | Thr | Ala | Gln | Arg | Ser | |
| 250 | | | | | 255 | | | | | 260 | | | | | 265 | |

```
ACT CTG CCC GAG GAA CTG AGC CTG GTC ATG GTG GAT AAC AAG ATC GAT      1443
Thr Leu Pro Glu Glu Leu Ser Leu Val Met Val Asp Asn Lys Ile Asp
            270                     275                 280

ACG ACA GAC TAC ACG GGC ATG CGC ACC AGT CTG TCG GGC GTC TAC GCC      1491
Thr Thr Asp Tyr Thr Gly Met Arg Thr Ser Leu Ser Gly Val Tyr Ala
        285                     290                 295

GTC GGT GAC TGC AAC AGT GAT GGA TCC ACG AAC GTG CCG CAT GCC ATG      1539
Val Gly Asp Cys Asn Ser Asp Gly Ser Thr Asn Val Pro His Ala Met
        300                     305                 310

TTC AGC GGA AAG AGA GCG GGT GTC TAT GTG CAT  G GTGAGCTCC             1583
Phe Ser Gly Lys Arg Ala Gly Val Tyr Val His
        315                     320

CTATACCTTC CTGTCTTCCG TTCTTTTTTT TTTTTCCCC CTTTCTTCCA TCCCTACCAT     1643

GAGATCTTGA ATGAAAGTCA ACTAACAAAA ACGTGTAG  TG GAA ATG TCC CGC        1695
                                             Val Glu Met Ser Arg
                                                              325

GAA GAG TCC AAC GCG GCC ATC TCC AAG CGC GAC TTC GAC AGA CGC GCC      1743
Glu Glu Ser Asn Ala Ala Ile Ser Lys Arg Asp Phe Asp Arg Arg Ala
330                     335                 340                 345

CTG GAG AAG CAA ACC GAG CGC ATG GTC GGC AAT GAG ATG GAG GAT CTG      1791
Leu Glu Lys Gln Thr Glu Arg Met Val Gly Asn Glu Met Glu Asp Leu
                350                     355                 360

TGG AAG CGC GTG CTG GAG AAC CAC CAC CGC CGG TCT TGAATCTTCC           1837
Trp Lys Arg Val Leu Glu Asn His His Arg Arg Ser
            365                     370

ATACTATATA CTAACGTCCT GTCCATGAAT AAACAACACG ACTAGCCACT ATGATATATA    1897

AATTTATATG TAACTAACGT TTAACGTCCT CCATGATCAT ATGGAGTGAC ACACATATTA    1957

ATACTTTCAC CAAGAAAAAT ACATACATAC ACACGCATTC GGTAATAAAA CATAGCTCCT    2017

GGGTATCTAC ATAGTAAGCA ATTCCGTAAC TCTAAATAAT GCCAACTCTA GTACTTGGAT    2077

TGCCAGGTTG GTAGGTTAGC TACTTCAGTA GTAACTGAAT CGACGCCCCC CAACAACAAA    2137

GTAAGTACCT CCTACCTCCC ACCCACTTTA CCAAGCACCC AGAAATCAAC AAATGAAAGA    2197

GAAATACGAT TAATAGTGAC AACCTGAAAT TACATTATAC AGGTCATATC GGCTTGTCTT    2257

GATTCGTACT TTTAGCTAAT ACCTTGTGAA ACTCCAAGAA TACTTGCAAC TCCTTGAGAC    2317

TGTGACTCGG AAGTTGTCTG GTCCAAATTA TATATATCGA CTACTAGTAG TAGCACTCTT    2377

CCAACAATAC TAGTAGTACC TAATGAATAG AACTATAGCT AAGATGTTAA AAGCATTGTA    2437

TGACTTTATT TGGGTTTATC TATACTACCG TAGTACTACT AGTTACTACG AGTTTGAATG    2497

GATAAATACT TACTGCTATA AAGGCCGAAG GGGGGTGGAT TGTGGGATGT TTCTGTGTCA    2557

GAATTC                                                              2563
```

( 2 ) INFORMATION FOR SEQ ID NO: 2:

( i ) SEQUENCE CHARACTERISTICS:
        ( A ) LENGTH: 392 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Ala Pro Lys Ser Leu Phe Tyr Ser Leu Phe Ser Thr Ile Ser Val
-19             -15                 -10                 -5

Ala Leu Ala Ser Ser Ile Pro Gln Thr Asp Tyr Asp Val Ile Val Val
                1           5                       10

Gly Gly Gly Pro Ala Gly Leu Ser Val Leu Ser Ser Leu Gly Arg Met
        15                  20                  25
```

```
Arg  Arg  Lys  Thr  Val  Met  Phe  Asp  Ser  Gly  Glu  Tyr  Arg  Asn  Gly  Val
 30                       35                      40                       45

Thr  Arg  Glu  Met  His  Asp  Val  Leu  Gly  Phe  Asp  Gly  Thr  Pro  Pro  Ala
                    50                       55                      60

Gln  Phe  Arg  Gly  Leu  Ala  Arg  Gln  Gln  Ile  Ser  Lys  Tyr  Asn  Ser  Thr
               65                       70                      75

Ser  Val  Ile  Asp  Ile  Lys  Ile  Asp  Ser  Ile  Thr  Pro  Val  Glu  Asp  Ala
               80                       85                      90

Ala  Ala  Asn  Ser  Ser  Tyr  Phe  Arg  Ala  Val  Asp  Ala  Asn  Gly  Thr  Gln
      95                      100                     105

Tyr  Thr  Ser  Arg  Lys  Val  Val  Leu  Gly  Thr  Gly  Leu  Val  Asp  Val  Ile
110                      115                     120                      125

Pro  Asp  Val  Pro  Gly  Leu  Arg  Glu  Ala  Trp  Gly  Lys  Gly  Ile  Trp  Trp
                    130                     135                          140

Cys  Pro  Trp  Cys  Asp  Gly  Tyr  Glu  His  Arg  Asp  Glu  Pro  Leu  Gly  Ile
                    145                     150                          155

Leu  Gly  Gly  Leu  Pro  Asp  Val  Val  Gly  Ser  Val  Met  Glu  Thr  His  Thr
          160                          165                     170

Leu  Tyr  Ser  Asp  Ile  Ile  Ala  Phe  Thr  Asn  Gly  Thr  Tyr  Thr  Pro  Ala
     175                          180                     185

Asn  Glu  Val  Ala  Leu  Ala  Ala  Lys  Tyr  Pro  Asn  Trp  Lys  Gln  Gln  Leu
190                           195                     200                      205

Glu  Ala  Trp  Asn  Val  Gly  Ile  Asp  Asn  Arg  Ser  Ile  Ala  Ser  Ile  Glu
                    210                     215                          220

Arg  Leu  Gln  Asp  Gly  Asp  Asp  His  Arg  Asp  Asp  Thr  Gly  Arg  Gln  Tyr
               225                     230                      235

Asp  Ile  Phe  Arg  Val  His  Phe  Thr  Asp  Gly  Ser  Ser  Val  Val  Pro  Asn
               240                     245                      250

Thr  Phe  Ile  Thr  Asn  Tyr  Pro  Thr  Ala  Gln  Arg  Ser  Thr  Leu  Pro  Glu
     255                      260                     265

Glu  Leu  Ser  Leu  Val  Met  Val  Asp  Asn  Lys  Ile  Asp  Thr  Thr  Asp  Tyr
270                      275                     280                           285

Thr  Gly  Met  Arg  Thr  Ser  Leu  Ser  Gly  Val  Tyr  Ala  Val  Gly  Asp  Cys
                    290                     295                          300

Asn  Ser  Asp  Gly  Ser  Thr  Asn  Val  Pro  His  Ala  Met  Phe  Ser  Gly  Lys
               305                     310                      315

Arg  Ala  Gly  Val  Tyr  Val  His  Val  Glu  Met  Ser  Arg  Glu  Glu  Ser  Asn
               320                     325                      330

Ala  Ala  Ile  Ser  Lys  Arg  Asp  Phe  Asp  Arg  Arg  Ala  Leu  Glu  Lys  Gln
     335                      340                     345

Thr  Glu  Arg  Met  Val  Gly  Asn  Glu  Met  Glu  Asp  Leu  Trp  Lys  Arg  Val
350                      355                     360                           365

Leu  Glu  Asn  His  His  Arg  Arg  Ser
                    370
```

( 2 ) INFORMATION FOR SEQ ID NO: 3:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO: 3:

```
Ser  Xaa  Ile  Pro  Gln  Thr  Asp  Tyr  Asp  Val  Ile  Val  Val  Gly  Gly  Gly
 1              5                        10                          15
```

Pro Ala Gly ( 2 ) INFORMATION FOR SEQ ID NO: 4:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO: 4:

Val Asp Asn Lys Ile Asp Thr Thr Asp Tyr Thr Gly
1               5                   10

( 2 ) INFORMATION FOR SEQ ID NO: 5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SOX07WM ( x i ) SEQUENCE DESCRIPTION: SEQ ID NO: 5:

GTRTARTCNG TNGTRTCNAT YTTRTTRTCN ACCAT 35

( 2 ) INFORMATION FOR SEQ ID NO: 6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SOX09WM ( x i ) SEQUENCE DESCRIPTION: SEQ ID NO: 6:

GTRTCNATYT TRTTRTCNAC CAT 23

( 2 ) INFORMATION FOR SEQ ID NO: 7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SOXTTT ( x i ) SEQUENCE DESCRIPTION: SEQ ID NO: 7:

GAGGATCCGT CGACTACTGA CTTTTTTTTT TTTTTTTTT 39

( 2 ) INFORMATION FOR SEQ ID NO: 8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
    ( A ) ORGANISM: SOXAAA ( x i ) SEQUENCE DESCRIPTION: SEQ ID NO: 8:

GAGGATCCGT CGACTACTGA C  21

( 2 ) INFORMATION FOR SEQ ID NO: 9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SOX24WM ( x i ) SEQUENCE DESCRIPTION: SEQ ID NO: 9:

CCATTGCATC CATTGAG  17

( 2 ) INFORMATION FOR SEQ ID NO: 10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SOX04WM ( i x ) FEATURE:
        ( A ) NAME/KEY: modified_base
        ( B ) LOCATION: group(9, 15)
        ( D ) OTHER INFORMATION: /mod_base=i
            / note="positions in sequence indicated by "N""

( x i ) SEQUENCE DESCRIPTION: SEQ ID NO: 10:

TGYATHCCNC ARACNGAYTA YGAYGT  26

( 2 ) INFORMATION FOR SEQ ID NO: 11:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: SOX05WM ( i x ) FEATURE:
        ( A ) NAME/KEY: modified_base
        ( B ) LOCATION: group(24, 30, 33, 36, 39, 42)
        ( D ) OTHER INFORMATION: /mod_base=i
            / note="Inosine postions indicated by "N""

( x i ) SEQUENCE DESCRIPTION: SEQ ID NO: 11:

ATYCCYCAGA CYGACTACGA CGTNATYGTN GTNGGNGGNG GNCCYGCYGG  50

( 2 ) INFORMATION FOR SEQ ID NO: 12:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
    ( A ) ORGANISM: SOX05WM ( i x ) FEATURE:
    ( A ) NAME/KEY: modified_base
    ( B ) LOCATION: group(24, 30, 33, 36, 39, 42)
    ( D ) OTHER INFORMATION: /mod_base=i
        / note="Inosine postions indicated by "N""

( x i ) SEQUENCE DESCRIPTION: SEQ ID NO: 12:

ATYCCYCAGA CYGACTACGA CGTNATYGTN GTNGGNGGNG GNCCYGCYGG     50

( 2 ) INFORMATION FOR SEQ ID NO: 13:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: SOX06WM ( i x ) FEATURE:
    ( A ) NAME/KEY: modified_base
    ( B ) LOCATION: group(9, 12, 18, 30)
    ( D ) OTHER INFORMATION: /mod_base=i
        / note="Inosine positions indicated by "N""

( x i ) SEQUENCE DESCRIPTION: SEQ ID NO: 13:

GTRTARTCNG TNGTRTCNAT YTTRTTRTCN ACCAT     35

( 2 ) INFORMATION FOR SEQ ID NO: 14:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: SOX08WM ( i x ) FEATURE:
    ( A ) NAME/KEY: modified_base
    ( B ) LOCATION: group(6, 18)
    ( D ) OTHER INFORMATION: /mod_base=i
        / note="inosine positions indicated by "N""

( x i ) SEQUENCE DESCRIPTION: SEQ ID NO: 14:

GTRTCNATYT TRTTRTCNAC CAT     23